United States Patent
Vrasidas et al.

(10) Patent No.: US 9,187,513 B2
(45) Date of Patent: Nov. 17, 2015

(54) N-SUBSTITUTED MANNOSAMINE DERIVATIVES, PROCESS FOR THEIR PREPARATION AND THEIR USE

(75) Inventors: Ioannis Vrasidas, Salonika (GR); Gyula Dekany, Sinnamon Park (AU); Ágnes Jánosi, Budapest (HU); Markus Hederos, Svedala (SE); Christoph Röhrig, Mühlingen (DE)

(73) Assignee: GLYCOM A/S, KGS. Lyngby (DK)

(*) Notice: Subject to any disclaimer, the term of this patent is extended or adjusted under 35 U.S.C. 154(b) by 0 days.

(21) Appl. No.: 14/111,131

(22) PCT Filed: Apr. 11, 2012

(86) PCT No.: PCT/IB2012/051759
§ 371 (c)(1),
(2), (4) Date: Nov. 4, 2013

(87) PCT Pub. No.: WO2012/140576
PCT Pub. Date: Oct. 18, 2012

(65) Prior Publication Data
US 2014/0046051 A1  Feb. 13, 2014

(30) Foreign Application Priority Data
Apr. 11, 2011  (GB) .................................. 1106095.1

(51) Int. Cl.
*C07H 1/00* (2006.01)
*C07H 5/06* (2006.01)
*C07H 15/18* (2006.01)
*C07H 13/04* (2006.01)

(52) U.S. Cl.
CPC .................. *C07H 5/06* (2013.01); *C07H 13/04* (2013.01); *C07H 15/18* (2013.01)

(58) Field of Classification Search
CPC ..................................... C07H 1/00; C07H 5/06
See application file for complete search history.

(56) References Cited

U.S. PATENT DOCUMENTS
2,884,411 A  4/1959  Heyns et al.

FOREIGN PATENT DOCUMENTS

| DE | 935 009 | 11/1955 |
|---|---|---|
| EP | 0 385 287 | 9/1990 |
| WO | 2007/135086 | 11/2007 |
| WO | 2010/029302 | 3/2010 |
| WO | 2010/061182 | 6/2010 |

OTHER PUBLICATIONS

International Search Report and Written Opinion mailed Aug. 13, 2012 in corresponding International Patent Application No. PCT/IB2012/051759.

Alessandro Dondoni et al., "Stereoselective Aminohomologation of Chiral α-Alkoxy Aldehydes via Thiazole Addition to Nitrones. Application to the Synthesis of N-Acetyl-D-Mannosamine," Tetrahedron Letters, vol. 33, No. 29, pp. 4221-4224 (1992).

Alessandro Dondoni et al., "Stereoselective Homologation-Amination of Aldehydes by Addition of Their Nitrones to C-2 Metalated Thiazoles-A General Entry to α-Amino Aldehydes and Amino Sugars," Chem. Eur. J., vol. 1, No. 8, pp. 505-520 (1995).

John C. Snowden et al., "2-Amino-2-deoxy-D-mannose Hydrochloride," Department of Chemistry, Washington University, St. Louis, Missouri, pp. 235-237 (undated).

Wolfgang Roth et al., "Methyl Derivatives of D-Mannosamine," Contribution from the Arthritis Research Laboratory, Departments of Medicine and Biochemistry, University of Alabama Medical Center, vol. 26, pp. 2455-2458 (Jul. 1961).

Eisuke Kaji et al., "Practical Syntheses of Immunologically Relevant β-Glycosides of 2-Acetamido-2-deoxy-D-mannopyranose. Methyl N-Acetyl-β-D-mannosaminide, N-Acetyl-β-D-mannosaminyl-(1→6)-D-galactose, and Methyl N-Acetyl-β-D-mannosaminyl-(1→4)-α-D-glucopyranoside," Bull. Chem. Soc. Jpn., vol. 61, pp. 1291-1297 (1988).

Shinya Yamaguchi et al., "Simple and Large-Scale Production of N-Acetylneuraminic Acid and N-Acetyl-D-Mannosamine," Trends in Glycoscience and Glycotechnology, vol. 18, No. 102, pp. 245-252 (Jul. 2006).

Rena Bodner et al., "α-N-Acetylmannosamine (ManNAc) Synthesis via Rhodium(II)-Catalyzed Oxidative Cyclization of Glucal 3-Carbamates," J. Org. Chem., vol. 70, pp. 3988-3996 (2005).

Jordi Calveras et al., "New chemo-enzymatic route toward N-acetylneuraminic acid derivatives with alkyl groups at C-7 hydroxyl group," Tetrahedron, vol. 66, pp. 4284-4291 (2010).

Kazuyoshi Takeda et al., "Synthesis of 2-Amino-2-deoxy-D-hexopyranosides from 4-O-Trichloroacetimidyl-D-hex-2-enopyranoside by [3, 3]-Sigmatropic Rearrangement," Tetrahedron Letters, vol. 33, No. 47, pp. 7145-7148 (1992).

Tanja M. Wrodnigg et al., "The Amadori and Heyns Rearrangements: Landmarks in the History of Carbohydrate Chemistry or Unrecognized Synthetic Opportunities?" Topics in Current Chemistry, vol. 215, pp. 115-152 (2001).

John F. Carson, "Reaction of Fructose with Benzylamine," Contribution from the Western Utilization Research Branch, Agricultural Research Service, United States Department of Agriculture, vol. 78, pp. 3728-3731 (Feb. 6, 1956).

Kurt Heyns et al., "The Implementation of Fructose and Sorbose with Ammonia and Amines," Chemical Reports, vol. 88, No. 10, pp. 1551-1555 (1955).

Peter S. Piispanen et al., "Improved Method for the Synthesis of 2-Alkylamino-2-deoxy-D-glucopyranose and 1,2-Dialkylamino-1,2-dideoxy-D-(N)-β-glucoside," J. Org. Chem., vol. 68, pp. 628-630 (2003).

Liqiang Chen et al., "Tandem reduction-reductive alkylation of azido sugars," Tetrahedron Letters, vol. 43, pp. 2705-2708 (2002).

Vince Pozsgay, "Stereoselective Synthesis of β-Mannosides," Carbohydrates in Chemistry and Biology, pp. 319-343 (2000).

(Continued)

*Primary Examiner* — Elli Peselev
(74) *Attorney, Agent, or Firm* — Pillsbury Winthrop Shaw Pittman LLP

(57) ABSTRACT

A compound of the formula (1) wherein $R_1$ is a group removable by hydrogenolysis, and wherein $R_2$ is OH or $R_2$ is —$NHR_3$ wherein $R_3$ is a group removable by hydrogenolysis. The compound can be made from fructose by a Heyns-rearrangement. The compound can be used then to make free D-mannosamine or its salts, D-mannosamine building blocks and mannosamine containing oligo- or polysaccharides, N-acetyl-D-mannosamine and its hydrates and solvates, neuraminic acid derivatives, and viral neuraminidase inhibitors.

23 Claims, No Drawings

(56) References Cited

OTHER PUBLICATIONS

Yoshisuke Tsuda et al., "Regio- and Stereo-Selective Transformation of Glycosides to Amino-glycosides: Practical Synthesis of Amino-sugars, 4-Amino-4-deoxy-D-galactose, 4-Amino-4-deoxy-L-arabinose, 3-Amino-3-deoxy-D-allose, 3-Amino-3-deoxy- D-glucose, 3-Amino-3-deoxy-D-ribose, 3-Amino-3-deoxy-D-xylose, 2-Amino-2-deoxy-D-mannose, and 5-Amino-5-deoxy-D-glucose (Nojirimycin)," Chem. Pharm. Bull., vol. 37, No. 10, pp. 2673-2678 (1989).

R. U. Lemieux et al., "The Synthesis of 2-Amino-2-Deoxysugars from Acetylated Glycals," Tetrahedron Letters, No. 26, pp. 2143-2148 (1965).

Hans Paulsen et al., "Erprobte synthese von 2-azido-2-desoxy-d-mannose und 2-azido-2-desoxy-d-mannuronsäure als baustein zum aufbau von bakterien-polysaccharid-sequenzen," Carbohydrate Research, vol. 136, pp. 153-176 (1985).

Andrea Vasella et al., "Convenient Synthesis of 2-Azido-2-deoxy-aldoses by Diazo Transfer," Helvetica Chimica Acta, vol. 74, pp. 2073-2077 (1991).

Therese Buskas et al., "Facile Preparation of Glycosyl Donors for Oligosaccharide Synthesis: 2-Azido-2-deoxyhexopyranosyl Building Blocks," Tetrahedron: Asymmetry, vol. 5, No. 11, pp. 2187-2194 (1994).

Harold J. Jennings, "Capsular Polysaccharides as Human Vaccines," Adv. Carbohydr. Chem. Biochem., vol. 41, pp. 155-208 (1983).

Ramesh K. Sood et al., "Capsular polysaccharide-protein conjugate vaccines," DDT, vol. 1, No. 9, pp. 381-387 (Sep. 1996).

Luciana Rovis et al., "Immunochemical Studies on a Mouse Myeloma Protein Having Specific Binding Affinity for 2-Acetamido-2-Deoxy-D-Mannose," Carbohydrate Research, vol. 23, pp. 223-227 (1972).

Tsu-Hsien at al., "Production of N-acetyl-D-neuraminic acid using two sequential enzymes overexpressed as double-tagged fusion proteins," BMC Biotechnology, vol. 9, No. 63, pp. 1-10 (2009).

Takeshi Sugai at al., "Improved Enzymatic Procedure for a Preparative-Scale Synthesis of Sialic Acid and KDN," Bull. Chem. Soc. Jpn., vol. 68, No. 12, pp. 3581-3589 (1995).

Dino K. Ress et al., "Sialic Acid Donors: Chemical Synthesis and Glycosylation," Current Organic Synthesis, vol. 1, No. 1, pp. 31-46 (2004).

Xi Chen et al., "Advances in the Biology and Chemistry of Sialic Acids," ACS Chemical Biology, vol. 5, No. 2, pp. 163-176 (2010).

Evan J. Horn et al., "Efficient Method for the Preparation of Peracetylated Neu5Ac2en by Flash Vacuum Pyrolysis," J. Org. Chem., vol. 74, No. 11, pp. 4357-4359 (2009).

Mark von Itzstein et al., "A convenient method for the introduction of nitrogen and sulfur at C-4 on a sialic acid analogue," Carbohydrate Research, vol. 244, pp. 181-185 (1993).

Peter S. Piispanen et al., "Surface Properties of Surfactants Derived from Natural Products. Part 1: Syntheses and Structure/Property Relationships-Solubility and Emulsification," Journal of Surfactants and Detergents, vol. 7, No. 2, pp. 147-159 (Apr. 2004).

Mark von Itzstein at al., "Rational design of potent sialidase-based inhibitors of influenza virus replication," Nature, vol. 363, pp. 418-423 (Jun. 3, 1993).

Andrew J. Humphrey et al. , "Biological Properties of N-Acyl and N-Haloacetyl Neuraminic Acids: Processing by Enzymes of Sialic Acid Metabolism, and Interaction with Influenza Virus", Bioorganic & Medicinal Chemistry 10 (2002) 3175-3185.

Toshihiko Toida, "C-2 Epimerization of N-Acetylglucosamine in an Oligosaccharide derived from Heparan Sulfate", J. Carbohydrate Chemistry, 15(3), (1996), 351-360.

N-SUBSTITUTED MANNOSAMINE DERIVATIVES, PROCESS FOR THEIR PREPARATION AND THEIR USE

CROSS REFERENCE TO RELATED APPLICATIONS

This application is the National Phase entry of PCT/IB2012/051759, which claims priority to Great Britain Patent Application No. 1106095.1, filed Apr. 11, 2011. The content of these applications is incorporated herein by reference in their entirety.

FIELD OF THE INVENTION

The present invention relates to the provision, synthesis and use of novel mannosamine derivatives.

BACKGROUND OF THE INVENTION

2-Amino-2-deoxy-D-mannose (D-mannosamine) mainly in its N-acetylated form (ManNAc) can be found as a building unit of some bacterial capsular polysaccharides and lipopolysaccharides. In addition, N-acetyl-D-mannosamine is the biosynthetic precursor of sialic acid, a unique nine-carbon ketoaldonic acid having many major biological roles.

One can obtain D-mannosamine or N-acetyl-D-mannosamine by means of chemical or enzymatic transformations. N-Acetyl-D-glucosamine can be converted into N-acetyl-D-mannosamine via 2-epimerization which can be initiated with bases (organic or inorganic bases as well as basic ion exchange resins are suitable) or epimerase enzymes [1-3]. In these methodologies an equilibrium between N-acetyl-D-glucosamine and N-acetyl-D-mannosamine is formed wherein the gluco compound is favoured, thus sophisticated and/or complicated separation techniques are needed to isolate this minor product from the starting material remaining, reagent and/or enzymes and other undesired by-products. The isolation difficulties, the moderate chemical yield and the relative expense of the starting compound all prevent this procedure being scaled-up in a cost-effective way. In classical synthetic methods, cheap and easily available simple monosaccharides can be transformed into the D-mannosamine framework like D-arabinose (stereoselective aminohomologation of D-arabinose chain via thiazole addition to nitrone [4,5], addition of ammonia to D-arabo-tetraacetoxy-1-nitro-1-hexene [6]), D-glucose (nucleophilic displacement of good leaving groups in C-2 with N-nucleophiles [7], stereoselective reduction of 2-gluculose oximes [8,9]) or D-glucal (intermolecular addition of nitrosyl chloride to the double bond [10], azidonitration of the double bond [11], intramolecular rhodium(II)-catalyzed oxidative cyclization of glucal-3-carbamates [12,13], [3,3]sigmatropic rearrangement of 4-O-trichloroacetimidyl-hex-2-enopyranosides derived from glucal [14]). These chemical pathways always stand in need of extensive use of protecting groups in order to mask functional groups that would be affected by the key transformational step(s), thus they consist of many elementary chemical steps. Such multistep sequences restrict usefulness and are not attractive for large scale developments because of the long technological time and the use of high number of reagents (which in fact, not uncommonly, can be toxic, of low availability and/or expensive) and/or require lengthy or cumbersome isolation/separation procedures.

Reaction of a ketose with an amine giving a ketosyl amine and the subsequent rearrangement of the latter into 2-amino-2-deoxy-aldose is known as Heyns-rearrangement [15]. Theoretically both 2-epimers can be formed, nevertheless the formation of one of the epimers is favoured, presumably because of steric factors. In the Heyns-rearrangement of D-fructose with a primary amine the exclusive formation of the corresponding gluco derivative is observed. Particularly, crystalline fructosyl benzyl amine, obtained as an intermediate by reacting D-fructose with benzyl amine, rearranges exclusively to 2-benzylamino-2-deoxy-D-glucose upon treatment with glacial acetic acid in methanol [16]. On the other hand, the formation of N-benzyl-2-benzylamino-2-deoxy-D-glucopyranosylamine was reported in the reaction of D-fructose with benzyl amine (the latter serves as reactant and solvent also) upon heating [17] or in the presence of a catalytic amount of benzyl ammonium chloride or $ZnCl_2$ [18,19].

The synthesis of N-alkyl- or N-(substituted alkyl)-mannosamine glycosides is possible in a tandem reduction-reductive alkylation reaction of 2-azido-2-deoxy-mannose derivatives in the presence of an alkanal or substituted alkanal [20].

The biological significance of mannosamine derivatives always provides an incentive for developing new, short and simple synthetic routes towards them that can be easily scaled-up. It is an aim of the present invention to provide such a method.

SUMMARY OF THE INVENTION

A first aspect of the present invention relates to N-substituted D-mannosamine derivatives of the following formula 1 and their salts

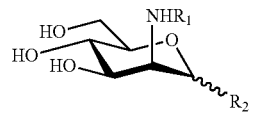

wherein $R_1$ is a group removable by hydrogenolysis, and wherein $R_2$ is OH or $R_2$ is —$NHR_3$ wherein $R_3$ is a group removable by hydrogenolysis.

Preferably, each of the $R_1$ and $R_2$ groups removable by hydrogenolysis is a benzyl or naphthylmethyl group optionally substituted with one or more phenyl, alkyl or halogen groups, more preferably a benzyl group.

Preferably, the compound has the following formula 1A

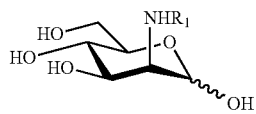

wherein $R_1$ is a group removable by hydrogenolysis, preferably a benzyl or naphthylmethyl group optionally substituted with one or more groups selected from phenyl, alkyl or halogen, more preferably a benzyl group;

or the following formula 1B

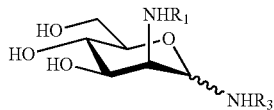

1B wherein $R_1$ and $R_3$ are each independently a group removable by hydrogenolysis, preferably a benzyl or naphthylmethyl group optionally substituted with one or more groups selected from phenyl, alkyl or halogen, and more preferably a benzyl group.

The second and third aspects of this invention relates to processes for the synthesis of N-substituted D-mannosamine derivatives of formula 1. Specifically:

The second aspect of the invention relates to N-substituted D-mannosamine derivatives of the following formula 1A

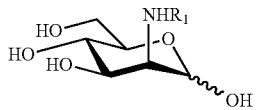

1A wherein $R_1$ is a group removable by hydrogenolysis,
are made by a first process comprising the steps of: a) treating D-fructose with $R_1$—$NH_2$, preferably benzyl amine, to yield a fructosyl amine derivative; b) isolating the fructosyl amine derivative as a crude product by separating excess $R_1$—$NH_2$ from it; and c) treating, preferably in methanol, the crude fructosyl amine derivative with acid, preferably glacial acetic acid, to produce a compound of formula 1A by a Heyns-rearrangement.

Preferably, the reaction time allowed for the step of treating D-fructose with $R_1$—$NH_2$ to yield a fructosyl amine derivative is at most 2 days, and more preferably at most 24 hours.

The third aspect of the invention relates to bis-N-substituted D-mannosamine derivatives of the following formula 1B

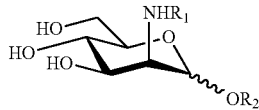

1B wherein $R_1$ and $R_2$ are each independently a group removable by hydrogenolysis,
are made by a process comprising the step of treating D-fructose with $R_1$—$NH_2$, preferably benzyl amine, to produce a compound of formula 1B by a Heyns-rearrangement. Preferably, D-fructose is treated with both $R_1$—$NH_2$ and a benzyl amine salt catalyst for a Heyns-rearrangement.

Preferably, the reaction time allowed for the step of treating D-fructose with $R_1$—$NH_2$ to yield a fructosyl amine derivative is at most four days, more preferably two days, and most preferably 24 hours.

Also according to the second and third aspects of this invention, a process is provided for forming a salt of a compound of formula 1 by converting the compound of formula 1A or 1B into its salt.

Further according to the second aspect of the invention is provided a method for the preparation of a compound of formula 1A, comprising the steps of: a) making a compound of formula 1B from D-fructose as described above; and b) and treating the compound of 1B with acid to remove the —$NHR_3$ group.

A fourth aspect of the invention relates to the use of a compound of formula 1 for the synthesis of free D-mannosamine or salts thereof.

A fifth aspect of the invention relates to the use of a compound of formula 1 for the synthesis of D-mannosamine building blocks and mannosamine containing oligo- or polysaccharides.

A sixth aspect of the invention relates to use of a compound of formula 1 for the synthesis of N-acetyl-D-mannosamine (ManNAc), O-glycosides thereof and hydrates or solvates thereof.

A seventh aspect of the invention relates to use of a compound of formula 1 for the synthesis of neuraminic acid derivatives and salts thereof or neuraminic acid containing oligo- or polysaccharides. Preferably, the neuraminic acid derivatives are sialic acid and salts thereof. Preferably, the neuraminic acid containing oligo- or polysaccharides are sialylated human milk oligosaccharides.

An eighth aspect of the invention relates to use of a compound of formula 1 for the synthesis of viral neuraminidase inhibitors. Preferably, the viral neuraminidase inhibitor is zanamivir.

A ninth aspect of the invention relates to a method of synthesizing D-mannosamine, comprising the step of hydrogenolysis of a compound of formula 1 to remove the $R_1$ and/or $R_3$ group(s). Preferably, the compound of formula 1 is made from D-fructose by the method of the second aspect of the invention.

A tenth aspect of the invention relates to a method of synthesizing a D-mannosamine-derived synthon, comprising the steps of:
i) synthesizing D-mannosamine according to the ninth aspect;
ii) carrying out a diazo transfer reaction of D-mannosamine to convert its amino group to an azido group;
iii) protecting the 3, 4 and 6 OH groups; and
iv) activating the anomeric position to obtain a β-mannosaminyl synthon.

An eleventh aspect of the invention relates to a method of synthesizing a D-mannosamine-derived synthon, comprising the steps of:
i) synthesizing D-mannosamine of the ninth aspect of the invention;
ii) masking the amino group of the D-mannosamine with a suitable protecting group;
iii) protecting the 3, 4 and 6 OH groups; and
iv) activating the anomeric position to obtain a β-mannosaminyl synthon.

A twelfth aspect of the invention relates to a method of synthesizing a D-mannosamine containing oligo- or polysaccharide, comprising the method of any one of the tenth and eleventh aspects followed by the additional step of:
v) coupling the β-mannosaminyl synthon to a desired sugar moiety.

A thirteenth aspect of the invention relates to a method of synthesizing ManNAc, comprising the steps of:
(i) synthesizing D-mannosamine according to the ninth aspect; and
(ii) acetylating the amine group of D-mannosamine to form ManNAc.

A fourteenth aspect of the invention relates to a method of synthesizing N-acetyl neuraminic acid, comprising the steps of:

(i) synthesizing ManNAc according to the thirteenth aspect; and (ii) reacting ManNAc with pyruvate in the presence of Neu5Ac aldolase.

A fifteenth aspect of the invention relates to a method of synthesizing sialooligosaccharides, comprising the steps of:

(i) synthesizing N-acetyl neuraminic acid according to the fourteenth aspect;

(ii) forming an activated sialoside from the N-acetyl neuraminic acid; and (iii) converting the activated sialoside to a sialooligosaccharide.

Preferably, the sialooligosaccharide is a sialylated human milk oligosaccharide.

A sixteenth aspect of the invention relates to a method of synthesizing a viral neuraminidase inhibitor, comprising the steps of:

(i) synthesizing N-acetyl neuraminic acid according to the fourteenth aspect;

(ii) protecting the carboxyl group as an ester and the non-glycosidic hydroxyl groups with acyl groups;

(iii) converting the glycosidic hydroxyl group into an aglycon and subjecting it to β-elimination to result in C2-C3 unsaturation;

(iv) introducing a nitrogen function at C4 with retention of configuration;

(v) deprotecting the carboxyl and hydroxyl groups; and (vi) converting the nitrogen function into an amino or guanidino group.

Preferably, the viral neuraminidase inhibitor is zanamivir.

A seventeenth aspect of the invention relates to the use of D-fructose in the synthesis of N-acetyl D-mannosamine or derivatives thereof.

An eighteenth aspect of the invention relates to the use of D-fructose in the synthesis of N-acetyl neuraminic acid or derivatives thereof.

A nineteenth aspect of the invention relates to a method of synthesis of N-substituted D-mannosamine derivatives substantially as described herein.

A twentieth aspect of the invention relates to a method of synthesis of neuraminic acid derivatives substantially as described herein.

A twenty-first aspect of the invention relates to a method of synthesis of viral neuraminidase inhibitors substantially as described herein.

DETAILED DESCRIPTION OF THE INVENTION

In accordance with this invention, the term "group removable by hydrogenolysis" refers to groups whose bond attached to the core carbohydrate structure can be cleaved by addition of hydrogen in the presence of catalytic amounts of palladium, Raney nickel or another appropriate metal catalyst known for use in hydrogenolysis, resulting in the regeneration of the protected functional group, mainly —OH or —NH$_2$ of the parent molecule. Such protecting groups are well known to the skilled man and are thoroughly discussed in P. G. M. Wuts and T. W. Greene: *Protective Groups in Organic Synthesis*, John Wiley & Sons (2007). Suitable protecting groups include, but are not limited to, benzyl, diphenylmethyl which can optionally be substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). Preferably, these groups are substituted or unsubstituted benzyl groups.

In connection with the possible substituents that are borne by a "group removable by hydrogenolysis" defined above and/or by some of the substituents themselves, the term "alkyl" means a linear or branched chain saturated hydrocarbon group with 1-6 carbon atoms, such as methyl, ethyl, n-propyl, i-propyl, n-butyl, i-butyl, s-butyl, t-butyl or n-hexyl; the term "aryl" refers to a homoaromatic group such as phenyl or naphthyl; the term "acyl" represents an R'—C(=O)-group, wherein R' can be H, alkyl (see above) or aryl (see above), such as formyl, acetyl, propionyl, butyryl, pivaloyl or benzoyl, and wherein the alkyl or aryl residue can either be unsubstituted or can be substituted with one or more groups selected from alkyl (only for aryl residues), halogen, nitro, aryl, alkoxy, amino, alkylamino, dialkylamino, carboxyl, alkoxycarbonyl, carbamoyl, N-alkylcarbamoyl, N,N-dialkylcarbamoyl, azido, haloalkyl or hydroxyalkyl, giving rise to acyl groups such as chloroacetyl, trichloroacetyl, 4-chlorobenzoyl, 4-nitrobenzoyl, 4-phenylbenzoyl, 4-benzamidobenzoyl, 4-(phenylcarbamoyl)-benzoyl, glycolyl or acetoacetyl; the term "alkyloxy" or "alkoxy" means an alkyl group (see above) attached to the parent molecular moiety through an oxygen atom, such as methoxy, ethoxy or t-butoxy; "halogen" means fluoro, chloro, bromo or iodo; "amino" refers to a —NH$_2$ group; "alkylamino" means an alkyl group (see above) attached to the parent molecular moiety through an —NH-group, such as methylamino or ethylamino; "dialkylamino" means two alkyl groups (see above), either identical or different ones, attached to the parent molecular moiety through a nitrogen atom, such as dimethylamino or diethylamino; "acylamino" refers to an acyl group (see above) attached to the parent molecular moiety through an —NH-group, such as acetylamino (acetamido) or benzoylamino (benzamido); "carboxyl" denotes an —COOH group; "alkyloxycarbonyl" means an alkyloxy group (see above) attached to the parent molecular moiety through a —C(=O)-group, such as methoxycarbonyl or t-butoxycarbonyl; "carbamoyl" is an H$_2$N—C(=O)-group; "N-alkylcarbamoyl" means an alkyl group (see above) attached to the parent molecular moiety through a —HN—C(=O)-group, such as N-methylcarbamoyl; "N,N-dialkylcarbamoyl" means two alkyl groups (see above), either identical or different ones, attached to the parent molecular moiety through a >N—C(=O)-group, such as N,N-methylcarbamoyl.

In accordance with the first aspect of this invention, N-substituted D-mannosamine derivatives of the following formula 1 and their salts are provided

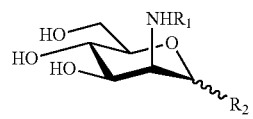

1 wherein R$_1$ is a group removable by hydrogenolysis and R$_2$ is OH (characterized as formula 1A) or R$_2$ is —NHR$_3$ wherein R$_3$ is a group removable by hydrogenolysis (characterized as formula 1B):

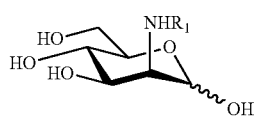

1A

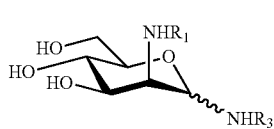

N-substituted D-mannosamine derivatives of formula 1 and salts thereof can be characterized as crystalline solids, oils, syrups, precipitated amorphous material or spray dried products. If crystalline, they can exist either in anhydrous or in hydrated crystalline forms by incorporating one or several molecules of water into their crystal structures. Similarly, N-substituted D-mannosamine derivatives of formula 1 and salts thereof can exist as crystalline substances incorporating ligands such as organic molecules and/or ions into their crystal structures. The N-substituted D-mannosamine derivatives of formula 1 and salts thereof includes anomeric mixtures of α- and β-anomers and/or the pure form of the α- or the β-anomers.

It should be emphasized that the N-substituted D-mannosamine derivatives of formula 1 can exist, both in solution and as solids, in cyclic hemiacetal form, especially pyranose and furanose forms (both having α- and β-anomers), as well as in open chain form. The relative proportion of the forms depends on the nature of the solvent(s), concentration, temperature and/or condition(s) under which solidification, precipitation, crystallization or other means of solvent removal is carried out.

Preferred $R_1$- and $R_3$-groups in compounds of formula 1 are, independently, benzyl or naphthylmethyl groups optionally substituted with one or more groups selected from phenyl, alkyl or halogen. More preferably, $R_1$ is benzyl, and also preferably $R_1$ and $R_3$ are identical in compounds of formula 1B. These preferred protecting groups have the advantage that the by-products of their hydrogenolysis are exclusively toluene, methylnaphthalene, or substituted toluene or methylnaphthalene derivatives, respectively. Such by-products can easily be removed even in multi-ton scales from water soluble saccharide products via evaporation and/or extraction processes.

In accordance with the second aspect of this invention, a process is provided for preparing N-substituted D-mannosamine derivatives of the following formula 1A and their salts

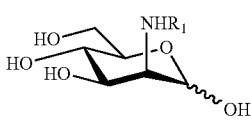

wherein $R_1$ is a group removable by hydrogenolysis.

This process comprises the steps of: a) treating D-fructose with $R_1$—$NH_2$ to yield a fructosyl amine derivative, b) isolating the fructosyl amine derivative as a crude product by separating excess $R_1$—$NH_2$ from it, and c) treating the crude product with an acid to obtain an N-substituted D-mannosamine derivative of formula 1A by a Heyns-rearrangement. In step a), fructose is reacted with an excess (preferably 3-10 equiv.) of a primary amine of formula $R_1$—$NH_2$. Preferably, the primary amine reagent is an optionally substituted benzyl amine or an optionally substituted naphthylmethyl amine, particularly benzyl amine. The primary amine reagent—if liquid—can also serve as a solvent, or a concentrated solution of the amine reagent in alcohol, dioxane, THF, DMF, or another suitable solvent can be used. Preferably, fructose is added to the amine reagent as solvent at about 0° C., and then the mixture is allowed to warm to room temperature or slowly heated up to 40° C., so that the starting material is consumed. The reaction is continued until consumption of the starting material is observed by TLC, which is typically observed within 24 h, usually within 18-20 hours. It has not been found necessary to allow the reaction to proceed for 4 days as described in ref [16].

In step b), the excess of primary amine reagent is removed from the crude fructosyl amine derivative before adding acid to initiate the rearrangement reaction c). Apolar solvents not dissolving the intermediate fructosyl amine derivative, mainly lower hydrocarbons such as pentanes, hexanes, heptanes or mixtures thereof such as petroleum ether are suitable to extract the amine reagent. As the fructosyl amine derivative formed in the reaction is poorly soluble in apolar solvents, the organic layer containing the amine reagent can be easily separated. Hence, any excess of the amine reagent is preferably washed away by using petroleum ether in step b). Preferably, the suspension/emulsion formed after addition of the apolar solvent is frozen at a temperature of between −20 and −25° C. and the supernatant organic phase is decanted. The supernatant organic phase is found not to contain any significant quantity of carbohydrate-like compound. The washing procedure can be repeated several times. The fructosyl amine derivative must not be precipitated and/or crystallized but should be used directly in step c). That is to say, the meaning of "isolating the fructosyl amine derivative as a crude product by separating excess of $R_1$—$NH_2$ from it" is that no purification of the fructosyl amine derivative should be carried out other than the removal of the excess amine reagent and any additional solvent used in step a). In particular, the fructosyl amine derivative must not be crystallised as in reference [16]. It has now been found that, in contrast to the report in reference [16], it is possible to obtain the manno-epimer (that is, the N-substituted D-mannosamine derivative) in step c) when using the crude product of step b), whereas the authors of reference [16], who purified the product of step a) by crystallisation, obtained exclusively the gluco-epimer (that is, the N-substituted D-glucosamine derivative) from treatment of the crystallised fructosyl amine derivative with acid. Without wishing to be bound by any theory, it is believed that the different reaction conditions, and the possible different intermediate compounds formed, existing during the Heyns-rearrangement of step c) as a result of the crystallisation of the intermediate in reference [16], and the removal of the amine without crystallisation of the intermediate in this invention leads to the different products obtained in these three circumstances.

In step c), the crude fructosyl amine derivative is dissolved in alcohol, dioxane, THF, DMF or a mixture thereof, preferably in alcohol, more preferably in methanol, and an acid is added to promote rearrangement of the fructosyl amine derivative. Preferably, in step c) the crude fructosyl amine derivative is taken up in methanol followed by addition of an acid. The acid can be used in any amount from a catalytic amount to a large excess. The acid can be an inorganic protic acid such as HCl, HBr, sulfuric acid or phosphoric acid, or an organic protic acid such as formic acid, acetic acid, oxalic acid, an optionally substituted methanesulphonic acid derivative, an optionally substituted benzenesulphonic acid derivative, a polymer bound sulphonic acid (i.e., an ion exchange resin), or a Lewis-acid such as $AlCl_3$, $ZnCl_2$, $CuBr_2$ or $BF_3$-etherate, preferably glacial acetic acid. The reaction typically takes place at room temperature and is completed within several hours, such as up to 8 hours, and preferably within 2-4 hours. Two main products are formed, with the major product being N-substituted-glucosamine and the minor component being N-substituted-mannosamine in a proportion of ca. 6:4 to 8:2. The total yield of the two products can be as high as 75-80% based on fructose. The products can be isolated by conventional separation techniques such as chromatography.

It has now been surprisingly found that the Heyns-rearrangement reaction of step c) can produce a considerable amount of the corresponding 2-amino-2-deoxy-D-mannose derivatives along with 2-amino-2-deoxy-D-glucose derivatives. The method thus represents a new way of constructing a mannosamine framework.

It is believed that the purified, crystallized fructosyl benzyl amine with a certain ring size, conformation and anomeric configuration used for the rearrangement reaction according to reference [16], as explained above, leads to the different outcome of the Heyns rearrangement in reference [16] from that of the present invention. Surprisingly, the work-up procedure of this invention in step b) results in practically no loss of the fructosyl amine derivative that is detectable in the washing procedure. It is believed that the crude fructosyl amine derivative obtained as a result of step b) comprises not a single specific conformer but a mixture of α- and β-pyranoses or furanoses in equilibrium, among which, it is proposed, some can be favourable precursors for the formation of the manno-compound.

According to the third aspect of the invention, a process is provided for the preparation of substituted 1,2-diamino-1,2-dideoxy-D-mannosamine derivatives and salts thereof of the following formula 1B

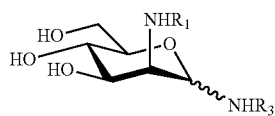

1B wherein $R_1$ and $R_3$ are each independently a group removable by hydrogenolysis.

This process comprises the steps of: a) treating D-fructose with $R_1$—$NH_2$ and a salt thereof, and b) separating the compound of formula 1B from the reaction mixture.

In step a), fructose is reacted with an excess (preferably 2-10 equiv., more preferably 3-4 equiv.) of a primary amine of formula $R_1$—$NH_2$ in the presence of a salt of the said primary amine. Preferably, the primary amine reagent is an optionally substituted benzyl amine or an optionally substituted naphthylmethyl amine, particularly benzyl amine. The primary amine reagent—if liquid—can also serve as a solvent, or a concentrated solution of the amine reagent in alcohol, dioxane, THF, DMF, or another suitable solvent can be used. The salt of $R_1$—$NH_2$ preferably refers to a halide, hydrogen phosphate, N-benzyl-carbamate, bicarbonate or carbonate salt, or carbon dioxide adduct of $R_1$—$NH_2$, more preferably benzyl ammonium chloride, and is used in 0.2-1.0 equivalents, preferably 0.3-0.4 equivalents in proportion to the parent amine. Preferably, fructose is added to the amine reagent with the amine reagent acting also as the solvent, followed by the addition of the salt of said amine reagent at about 20-30° C. Alternatively, fructose is added to the mixture of the amine reagent and its salt. The reaction is continued until consumption of the starting material as monitored by TLC, which is typically observed within four days, usually within 48 h, and preferably within 24 hours. It has not been found necessary to allow the reaction to proceed for 1 month as described in ref [18]. It has been found by the present inventors that if the reaction is continued for more than four days the yield of the manno-epimer decreases to below a commercially-acceptable level, and isolation of the eventual product is more difficult.

It has then been found that, in contrast to the report in references [17-19], it is possible to obtain a significant amount of the manno-epimer (that is, the N,N'-disubstituted 1,2-diamino-1,2-dideoxy-D-mannosamine derivative) under the circumstances disclosed above, whereas the authors of reference [17-19] obtained exclusively the gluco-epimer (that is, the N,N'-disubstituted 1,2-diamino-1,2-dideoxy-D-glucosamine derivative). At the end of step a), two main products are formed, with the major product being the N,N'-disubstituted 1,2-diamino-1,2-dideoxy-D-glucosamine derivative and the minor component being the N,N'-disubstituted 1,2-diamino-1,2-dideoxy-D-mannosamine derivative in a proportion of ca. 6:4 to 7:3. The total yield of the two products can be as high as 75-100% based on fructose. In step b) the two isomers are separated by precipitation, crystallization or chromatography. Preferably, in step b) water or aqueous alcohol solution is added to precipitate or crystallize the compound of formula 1B from the reaction mixture, while the gluco-isomer of compound of formula 1B remains in the mother liquor. It is, in the experience of the present inventors, unexpected that a minor epimer can be crystallised or precipitated from a mixture of a minor and a major epimer, while leaving the major epimer in solution.

A compound of formula 1B can be easily converted into a compound of formula 1A by treatment with an acid to remove the acid labile —$NHR_3$ group and regenerate the anomeric OH. In this reaction water—which is present in the reaction milieu as reagent—may serve as solvent or co-solvent as well. Organic protic or aprotic solvents which are stable under acidic conditions and miscible fully or partially with water such as $C_1$-$C_6$ alcohols, acetone, THF, dioxane, ethyl acetate, MeCN, etc. may be used in a mixture with water. The acids used are generally inorganic protic acids selected from but not limited to acetic acid, trifluoroacetic acid, HCl, formic acid, sulphuric acid, perchloric acid, oxalic acid, p-toluenesulfonic acid, benzenesulfonic acid and cation exchange resins, and organic acids including but not limited to acetic acid, formic acid, chloroacetic acid and oxalic acid, which may be present in from catalytic amount to large excess. The hydrolysis may be conducted at temperatures between 20° C. and reflux until reaching completion which takes from about 2 hours to 3 days depending on temperature, concentration and pH. Preferably, the hydrolysis is performed in an alcohol, more preferably in methanol or ethanol, by addition of concentrated HCl or diluted HCl-solution, and the pH is kept at around 3-4. Under such conditions the hydrolysis is typically complete within 2-3 hours at room temperature.

Where it is desired to produce a salt of one of the N-substituted D-mannosamine derivatives of formula 1A or 1B, the derivative can be converted into its acid addition salt in a conventional manner, using inorganic or organic acids or salts. Solvents such as acetone, water, dioxane, DMSO, THF, DMF, alcohols, MeCN, and mixtures thereof and inorganic acids such as HCl, $H_2SO_4$, $HNO_3$ and $H_3PO_4$, in concentrated form or diluted in water or other solvents, such as methanol, ethanol or dioxane, can be used. Organic acids such as formic acid, acetic acid, and oxalic acid can also be used. The salts of these acids with a base whose basicity is weaker than that of mannosamine can be used as well. Products are typically obtained by selective precipitation by adding apolar solvents such as diethyl ether, diisopropyl ether, acetone or alcohols, or by crystallization in high yield without any chromatography.

The cheap materials used and the simple and short technological actions applied in the Heyns reactions of the second and third aspects of the invention open the possibility to develop an upscalable, cost-efficient method for making mannosamine, which is a sugar building block currently having low availability. In addition, the by-product glucosamine is also a valuable sugar derivative of great importance.

The fourth aspect of this invention relates to the use of substituted D-mannosamine derivatives of formula 1 and salts thereof for the synthesis of free D-mannosamine and/or salts thereof. The method is based upon the utilisation of substituted D-mannosamine derivatives of formula 1 and salts thereof, wherein the $R_1$ (and optionally $R_3$) is removed by hydrogenolysis in a catalytic hydrogenation reaction (Scheme 1). This reaction typically takes place in a protic solvent or in a mixture of protic solvents. The protic solvent can be water, acetic acid or a $C_1$-$C_6$ alcohol. A mixture of one or more protic solvents with one or more suitable aprotic organic solvents partially or fully miscible with the protic solvent(s) (such as THF, dioxane, ethyl acetate or acetone) can also be used. Water, one or more $C_1$-$C_6$ alcohols, or a mixture of water and one or more $C_1$-$C_6$ alcohols are preferably used as the solvent system. Solutions containing the carbohydrate derivatives in any concentration or suspensions of the carbohydrate derivatives in the solvent(s) used are also applicable. The reaction mixture is stirred at a temperature in the range of 10-100° C., preferably between 20-50° C., in a hydrogen atmosphere of 1-50 bar absolute (100 to 5000 kPa) in the presence of a catalyst such as palladium, Raney nickel or any other appropriate metal catalyst, preferably palladium on charcoal or palladium black, until reaching the completion of the reaction. Transfer hydrogenation can also be performed, when the hydrogen is generated in situ from cyclohexene, cyclohexadiene, formic acid or ammonium formate. Addition of organic or inorganic bases or acids and/or basic and/or acidic ion exchange resins can also be used to improve the kinetics of the hydrogenolysis. The use of basic substances is especially preferred when starting from a compound of formula 1A when halogen substituents are present on the substituted benzyl moieties of the precursors and/or the formation of mannosamine base is desirable. Preferred organic bases include, but are not limited to, triethylamine, diisopropyl ethylamine, ammonia, ammonium carbamate and diethylamine. An organic or an inorganic acid is favourably used as a co-solvent or additive in cases when mannosamine salts are the intended products. Preferred acids include, but are not limited to, formic acid, acetic acid, propionic acid, chloroacetic acid, dichloroacetic acid, trifluoroacetic acid, HCl and HBr. When starting from a compound of formula 1B, an acid must be used, while the hydrolysis and the hydrogenolysis simultaneously take place. The conditions proposed above allow simple, convenient and delicate removal of the solvent(s) giving rise to pure mannosamine or its salt.

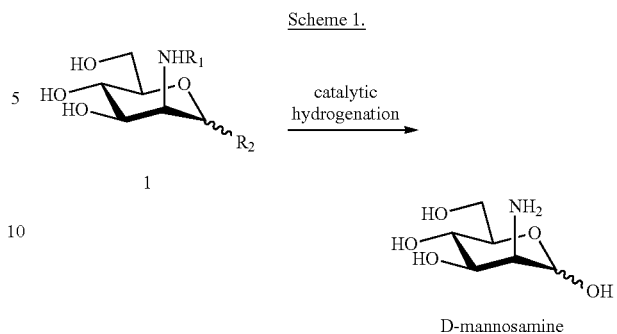

Scheme 1.

D-mannosamine

If mannosamine in the form of its free base is formed in the reductive step it can be converted into its acid-addition salt. The salt formation is typically carried out in solution using inorganic or organic acids or salts. Solvents including, but not limited to, acetone, water, dioxane, DMSO, THF, DMF, alcohols, MeCN, and mixtures of thereof can be used for such a transformation. Suitable inorganic acids include, but are not limited to, HCl, $H_2SO_4$, $HNO_3$ and $H_3PO_4$, in concentrated form or diluted in water or other solvents such as methanol, ethanol or dioxane. Suitable organic acids include, but are not limited to, formic acid, acetic acid and oxalic acid. The salts of these acids with a base whose basicity is weaker than that of mannosamine can be used as well. The product is typically obtained by selective precipitation by adding apolar solvents such as diethyl ether, diisopropyl ether, acetone or alcohols, or by crystallization in high yield. Chromatography is not necessary.

In a preferred embodiment, compounds of formula 1A or 1B, wherein $R_1$ and $R_3$ are benzyl or naphthylmethyl groups optionally substituted with one or more groups selected from phenyl, alkyl or halogen, and more preferably wherein $R_1$ and $R_3$ are benzyl groups, are used for the synthesis of free D-mannosamine and/or salts thereof. These preferred and more preferable protecting groups have the advantage that the by-products of the hydrogenolysis are exclusively toluene, methylnaphthalene, or substituted toluene or methylnaphthalene derivatives, respectively. Such by-products can easily be removed even in multi ton scales from water soluble saccharide products via evaporation and/or extraction processes.

According to another embodiment, the mixture of N-benzyl/substituted benzyl-D-mannosamine and -glucosamine obtained according to the second or third aspects, or the mixture of N,N'-disubstituted 1,2-diamino-1,2-dideoxy-D-mannosamine and -glucosamine obtained according to the third aspect is subjected to catalytic hydrogenolysis in the presence of acid, preferably HCl, to yield a mixture of D-mannosamine hydrochloride and D-glucosamine hydrochloride from which the components can be separated by selective crystallization leading to pure D-glucosamine hydrochloride and pure D-mannosamine hydrochloride.

The fifth aspect of this invention relates to the use of substituted D-mannosamine derivatives of formula 1 and salts thereof for the synthesis of D-mannosamine building blocks (that is, mannosamine derivatives that can be used for the synthesis of mannosamine-containing compounds such as oligo- or polysaccharides) and for the manufacture of mannosamine containing oligo- or polysaccharides.

N-Acetyl-D-mannosamine in oligo- or polysaccharides is preferably linked with a β-linkage. In order to achieve a β-interglycosidic link, two main routes have been developed: an indirect route in which glucopyranosyl, gluculopyranosyl or gluculopyranosyl oxime donors are first used to build the β-linkage and the reconstruction of the mannosamine unit is made after the formation of the β-linkage; and a direct route in which a suitable D-mannosaminyl donor is employed [21]. The latter route requires a non-participating group in position 2 of the D-mannosaminyl donor, and among such possible synthons only 2-azido-2-deoxy-D-mannopyranosyl derivatives have proved to have synthetic relevance. These glycosyl donors can be synthetized via complicated multistep pathways starting from D-glucose. However, the substituted D-mannosamine derivatives of formula 1 and salts thereof of the present invention can easily be converted into such mannosaminyl donors. Thus, the free amine, obtained by removal of the $R_1$-group, and optionally the $R_3$-group, according to the fourth aspect of the invention, can be subjected to a diazo transfer reaction with triflic azide to covert the amino group to azido [22]. This conversion can also be performed on mannosamine O- or S-glycosides that are suitable for glycosyl coupling (e.g. alkyl or aryl thioglycosides, O-pentenyl glycoside, see ref. [23]). Furthermore, the availability of the free mannosamine opens the way to mask the amino group before glycosylation reactions. Suitable protective groups can be, for instance, phthalyl, tetrachlorophthalyl, dithiasuccinoyl, trifluoroacetyl, trichloroacetyl, dimethylmaleolyl, trichloroethoxycarbonyl or allyloxycarbonyl group, all of which are readily used in glycosylation reactions. These groups can be introduced by the reaction of the amine with the activated acyl derivatives, such as anhydrides, halogenides or active esters, in the presence of a base, except for the dithiasuccinoyl group which can be formed via a two-step sequence (ethoxythiocarbonylation followed by cyclization with chlorocarbonylsulfenyl chloride). The resulting 2-azido- or 2-acylamino-2-deoxy-D-mannopyranose derivatives can be subjected to reactions to protect the 3,4,6-positions (ethers, esters, acetals) and after appropriate anomeric activation (thioglycosides, acetates, benzoates, trichloroacetimidates, glycosyl halides) they are considered to be useful synthons in interglycosidic coupling reactions to transfer β-mannosaminyl moiety.

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used for the synthesis of mannosamine which is then subsequently converted into D-mannosamine building blocks practical for the manufacture of mannosamine containing oligosaccharides.

A further embodiment relates to the use of substituted D-mannosamine derivatives of formula 1 and salts thereof for the synthesis of D-mannosamine containing oligosaccharides. Some pathogenic bacteria like *Neisseria meningitidis*, *Haemophylus influenzae* or *Streptococcus pneumoniaie* have capsular polysaccharides that contain 2-acetamido-2-deoxy-β-D-mannopyranosyl or -mannopyranuronic acid structural units (see e.g. ref. [24]). The recognition that the capsular polysaccharides present on the surface of bacteria are associated with the bacteria's virulence factor led to development of capsular polysaccharide vaccines licensed for the use in the immunoprophylaxis of diseases caused by the above-named microorganisms [25]. The chemical synthesis of these antigens requires the introduction of the mannosaminyl unit into a certain position of the oligo- or polysaccharide chain. After anomeric activation, the mannosaminyl building blocks obtained from substituted D-mannosamine derivatives of formula 1 and salts thereof by hydrogenolysis and subsequent conversion to suitable glycosyl donors as described above are allowed to react with an appropriate acceptor under glycosylation conditions. The term "glycosylation conditions" means in the present context to run the reaction in an aprotic solvent or in a mixture of aprotic solvents in the presence of an activator so as to lead to the desired glycosylated product by controlling the stereoselectivity of the conjugation via non-neighbouring group active protecting group strategy, solvent effect, halide effect, promoter selection and temperature control. In the case of carbohydrates, an array of anomeric activation and promoter design for glycosylation has been developed and is available to a skilled person engaged in synthetic carbohydrate chemistry. These methodologies are expansively discussed by reviews and handbooks, for instance by A. V. Demchenko (ed.): *Handbook of Chemical Glycosylation*, Wiley-VCH, 2008. For completeness, some general considerations are briefly mentioned below depending on the anomeric substituent (the protecting groups of the acceptors and donors remain intact under glycosylation).

The glycosyl halides (aglycon means F, Cl, Br, I) are frequently used in glycosylation reaction because of their easy accessibility and satisfactory reactivity. Typically, anomeric halides follow the reactivity order F<Cl<Br<I for nucleophilic displacement. The glycosylation reactions are generally promoted by heavy metal ions, mainly mercury or silver, and Lewis acids. Glycosyl trichloroacetimidates (aglycon is —OC(=NH)CCl$_3$) in typical glycosylation reactions can be promoted by catalytic amount of Lewis acid, such as trimethylsilyl triflate or BF$_3$-etherate. Glycosyl acetates or benzoates (aglycon represents —OAc or —OBz) in glycosylation reactions are first subjected to electrophilic activation providing a reactive intermediate, then treated with the nucleophilic OH-acceptor. Typical activators of choice are Brønsted acids (such as p-TsOH, HClO$_4$ or sulfamic acid), Lewis acids (such as ZnCl$_2$, SnCl$_4$, triflate salts, BF$_3$-etherate, trityl perchlorate, AlCl$_3$ or triflic anhydride) and their mixtures. Pentenyl glycosides (aglycon means —O—(CH$_2$)$_3$—CH=CH$_2$) as glycosyl donors can be transglycosylated with appropriate glycosyl acceptors in the presence of a promoter such as NBS or NIS. Protic or Lewis acids (triflic acid, Ag-triflate, etc.) can enhance the reaction. Thioglycosides (aglycon denotes alkylthio- or optionally substituted phenylthio-group) can be activated by thiophilic promoters such as mercury(II) salts, Br$_2$, I$_2$, NBS, NIS, triflic acid, triflate salts, BF$_3$-etherate, trimethylsilyl triflate, dimethyl-methlythio sulphonium triflate, phenylselenyl triflate, iodonium dicollidine perchlorate, tetrabutylammonium iodide or mixtures thereof, in condensation reactions, preferably by Br$_2$, NBS, NIS or triflic acid.

In order to construct oligo- or polysaccharides, the mannosaminyl containing structural disaccharide unit obtained above needs to be transformed further. These reactions can involve selective protection/deprotection manipulations of the OH-groups, the conversion of the azido or protected amino group to N-acetyl, anomeric activation of the reducing end for additional cross-coupling with acceptors, and optionally the selective oxidation of the primary OH-group in the mannosamine unit in the case of 2-acetamido-2-deoxy-β-D-mannopyranuronic acid residue containing oligomers, depending on whether the synthons will be used as donor, acceptor or both. These reactions are within the routine skill of a practitioner trained in carbohydrate chemistry, and discussed or summarized by numerous handbooks and reviews, e.g. S. Hanessian: *Preparative Carbohydrate Chemistry*, Marcel Dekker, 1997; M. L. Sinnot: *Carbohydrate Chemistry and Biochemistry*, RSC Publishing, 2007; D. E. Levy, P. Fügedi (eds.): *The Organic Chemistry of Sugars*, Taylor & Francis, 2006; T. K. Lindhorst: *Essentials of Carbohydrate Chemistry and Biochemistry*, Wiley-VCH, 2007.

In a preferred embodiment compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used for the synthesis of D-mannosamine containing oligosaccharides. This synthesis comprises the steps of reduction of the compound of formula 1 as defined above to mannosamine, subsequent conversion of the mannosamine into D-mannosamine building blocks, glycosylation reaction between the building blocks and appropriate glycosyl acceptors, and further functional group manipulations, glycosylation reactions and deprotection in order to give rise to D-mannosamine containing oligosaccharides.

The sixth aspect of this invention relates to the use of substituted D-mannosamine derivatives of formula 1 and salts thereof for the synthesis of N-acetyl-D-mannosamine (ManNAc) and its O-glycosides. N-Acetyl-D-mannosamine is of high importance as being the biosynthetic precursor of sialic acid. Furthermore, ManNAc and its methyl α- and β-glycosides, both as pyranoside and furanoside, have been proved to trigger antibody-like activity of immunoglobulin derived from mouse plasmacytoma [26].

In the prior art production of N-acetyl-D-mannosamine starting from N-acetyl-D-glucosamine by epimerization, initiated with either base or epimerase enzyme, an equilibrium mixture is reached, which poses isolation and purification problems. This problem can be overcome using substituted D-mannosamine derivatives of formula 1 provided by this invention, which can be reduced with catalytic hydrogenation (see above the fourth aspect) and the resulting mannosamine can be transformed into the N-acetyl derivative in two ways (Scheme 2). The first method is selective N-acetylation in the presence of one or more hydroxyls, which is a well-known reaction within the skilled person's general knowledge. It involves treatment of the mannosamine with acetic anhydride, acetyl halogenide or another appropriate acetyl transfer reagent known in the art, typically acetic anhydride or acetyl chloride. The reaction can be carried out in solution in the presence or absence of a base. Solvents including, but not limited to, acetone, water, dioxane, DMSO, THF, DMF, alcohols, MeCN, and mixtures thereof can be used for such a chemical transformation. A suitable base for use in the reaction is an inorganic base (such as $K_2CO_3$, $Na_2CO_3$ or $NaHCO_3$) or an organic base (such as pyridine, triethylamine or Hünig's base). The set temperature of the reaction can be between −10° C. up to the reflux temperature of the solvent(s). The reaction time typically varies from 30 min to 2 days depending on the structures, the set temperature and the nature of the reactive agent. The skilled practitioner knows how to drive the reaction in order to acetylate the amino portion while the OH-groups remain unaffected. Any eventually formed overacetylated by-product(s) can be readily transformed into ManNAc with e.g. NaOH/MeOH or NaOMe/MeOH treatment. The second method is a peracetylation followed by a de-O-acetylation. The peracetylation can be carried out in solution with an acylating agent in the presence or absence of a base. Solvents including, but not limited to, acetone, dioxane, DMSO, THF, DMF, alcohols, MeCN, and mixtures thereof can be used for such a chemical transformation. A suitable base for use in the reaction is an inorganic base (such as $K_2CO_3$, $Na_2CO_3$, $NaHCO_3$ or NaOH) or an organic base (such as pyridine, triethylamine or Hünig's base). A suitable acylating agent is an activated acetic acid derivative known in the art, and typically acetic anhydride and acetyl chloride are used as the acylating agent. The set temperature of the reaction can be between −10° C. up to the reflux temperature of the solvent(s). The reaction time typically varies from 30 min to 2 days depending on the structures, the set temperature, and the nature of the reactive agent. The skilled person knows how to drive the reaction until all of the functional groups are acetylated. The de-O-acetylation reaction can be carried out in solution in the presence of a base. If the base used for the reaction is an inorganic strong base (such as $K_2CO_3$, LiOH, NaOH, KOH or $Ba(OH)_2$), the solvents of choice are water, alcohol or water-organic solvent (such as acetone, dioxane, DMSO, THF, DMF, alcohols, MeCN) mixture. If an alcoholate (such as NaOMe, NaOEt or KO$^t$Bu) is chosen as the base, the solvent needs to be the corresponding alcohol (e.g. NaOMe/MeOH). The set temperature of the reaction can be between 0° C. up to the reflux temperature of the solvent(s). The reaction time typically varies from 30 min to 1 day depending on the structures, the set temperature, and the nature of the reactive agent.

Scheme 2.

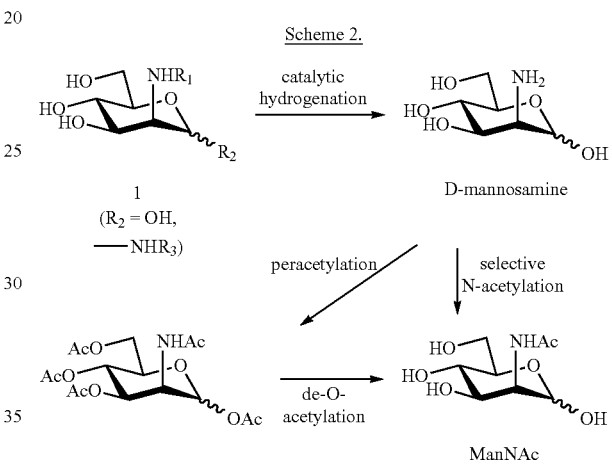

The reduction-acetylation sequence can be performed in separate elementary steps with the isolation of the intermediate free mannosamine in crystalline form, or conducted in one pot with the acetylation of the crude debenzylated mannosamine. Both methods provide pure crystalline N-acetylmannosamine in high yield. If desired, N-acetylmannosamine can be converted into the corresponding O-glycoside in a known manner.

In a preferred use compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine and acetylated to ManNAc.

The seventh aspect of this invention relates to the use of substituted D-mannosamine derivatives of formula 1 and salts thereof for the synthesis of neuraminic acid derivatives, including sialic acid and salts thereof, and sialic acid or other neuraminic acid containing oligo- or polysaccharides.

Neuraminic acids are derivatives of the nine-carbon sugar 5-amino-3,5-deoxy-D-glycero-D-galacto-nonulosonic acid, particularly N-acetyl-(Neu5Ac) and N-glycolyl-neuraminic acid (Neu5Gc), which can be substituted at C-4, C-7, C-8 and C-9 by various moieties. They have many major biological roles, ranging from embryogenesis to neural plasticity to pathogen interactions. Although they can rarely occur in free form, they are usually found in chemical covalent linkage at the non-reducing terminus or in internal positions of oligosaccharide side-chains of glycoproteins and glycolipids.

The linkages of sialic acids in which they are bound to penultimate sugars such as galactose, N-acetyl-galactosamine and N-acetyl-glucosamine are most commonly α-2,3- and α-2,6-ketosidic bonds.

N-Acetyl-neuraminic acid is commonly produced by enzymatic pathways, either from ManNAc and pyruvate by means of a Neu5Ac aldolase or in a two-enzyme sequential system where N-acetylglucosamine is epimerized on the action of a GlcNAc 2-epimerase and the in situ obtained ManNAc reacts further with pyruvate in the presence of a Neu5Ac aldolase (see e.g. ref. [27] and references cited therein).

N-Acetylmannosamine provided according to the sixth aspect of the invention in high purity can be used in the manufacture of neuraminic acid derivatives, preferably Neu5Ac, in enzymatic system. Generally, the aldol condensation is performed with a large, usually 7-10 fold, excess of pyruvate in order to drive the reaction toward product formation and maximize the consumption of ManNAc. The reaction can also be conducted in a continuous reactor. The product is mainly isolated by ion exchange chromatography from the unreacted ManNAc and pyruvate. The isolation steps can be simplified with the use of pyruvate decarboxylase, which catalyses the decomposition of excess pyruvic acid into the volatile acetaldehyde and carbon dioxide [28]. The resulting Neu5Ac can be transformed into other naturally occurring neuraminic acid derivatives by common chemical modifications. Moreover, as the aldolase enzyme accepts a broad range of substrates, mannosamine, N-glycolylmannosamine or other mannosamine derivatives, all of them available by simple conversion starting from substituted D-mannosamine derivatives of formula 1 and salts thereof, can serve as basis for synthesizing many natural and non-natural neuraminic acid derivatives by enzymatically directed aldol condensation reactions.

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine, acetylated to N-acetylmannosamine and allowed to react with pyruvate in the presence of Neu5Ac aldolase to form N-acetyl-neuraminic acid.

A further embodiment of this invention relates to the use of substituted D-mannosamine derivatives of formula 1 and salts thereof for the synthesis of neuraminic acid derivatives containing oligo- or polysaccharides, preferably sialoglycoconjugates.

Among sialoglycoconjugates, sialylated human milk oligosaccharides like 3'-sialyllactose, 6'-sialyllactose, 3'-sialyl-3-fucosyllactose, sialyllacto-N-tetraoses, sialyl-fucosyl-lacto-N-tetraoses, disialyllacto-N-tetraose, sialyllacto-N-fucopentaose, monosialyllacto-N-hexaose, monofucosyl-monosialyllacto-N-hexaose, mono fucosyl-monosialyllacto-N-neohexaose, mono fucosyl-disialyllacto-N-neohexaose etc. are of great importance which is directly linked to their unique biological activities such as antibacterial, antiviral, immune system and cognitive development enhancing activities. Sialylated human milk oligosaccharides are found to act as prebiotics in the human intestinal system helping to develop and maintain the intestinal flora. Furthermore they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics. In the human milk oligosaccharides the sialic acid residue is always linked to the terminal 3-O- and/or 6-O-position(s) of D-galactose via α-glycosidic linkage.

Generally, the synthesis of complex sialooligosaccharides follows multistep synthetic pathways, is conducted in enzymatic systems or combines both. Whatever route is taken, neuraminic/sialic acid derivatives suitably armed with protective groups and activated on the anomeric centre or neuraminyl/sialyl glycosides that are substrates for enzymes capable of transferring neuraminyl/sialyl moiety are needed in order to couple them to the host molecule.

Accordingly, substituted D-mannosamine derivatives of formula 1 and salts thereof are reduced to mannosamine, then acetylated to N-acetylmannosamine or transformed to other derivatives that are substrates for aldolase, are allowed to react with pyruvate in the presence of aldolase to form N-acetyl-neuraminic acid or other neuraminic acid derivatives as disclosed above, which then can be converted into the desired sialyl/neuraminyl donors by known methodologies. In chemical glycosylation, the secondary OH-groups, the amino grouping and the carboxylic portion have to be in protected form for which purpose an array of protecting groups, mainly esters, ethers and acetals, are available to the skilled person. Among OH—protection possibilities, optionally substituted acyls, such as acetyl, benzoyl, chloroacetyl or chlorobenzoyl, and ether-type groups such as benzyl are of synthetic usefulness; the carboxyl group can be protected by an ester, typically by a methyl or benzyl ester; and the amino function can be masked in form of an azide, diacetyl, trifluoroacetyl, trichloroacetyl, Troc, Fmoc or phthalimido group, or as a cyclic carbamate with the adjacent 4-OH. The anomeric centre substitution can be varied among halo, alkyl- or arylthio, dialkyl phosphite or trihaloacetimidate, each of which is commonly used in sialoglycosylation methods. The protective group introduction and anomeric centre activations mentioned above can be carried out by known processes (see e.g. refs. [29, 30] and references cited therein). The skilled man involved in carbohydrate chemistry, especially in sialochemistry, is able to select which protective groups and anomeric agylcons in the sialic donor are suitable in order to conduct the glycosylation reaction with the high probability of a preferable outcome including yield, anomeric ratio and by-product formation. These factors depend on promoter design, solvent effect, reaction condition, acceptor structure, etc. For enzymatic sialotransfer processes the appropriate substrates for the enzymes (e.g. CMP-sialic acid for sialyltransferases, 2-O-(p-nitrophenyl)- or 2-O-(4-methylumbelliferyl)-α-D-sialosides for transsialidases) are easily accessible from the neuraminic/sialic acid derivatives obtained by the above method.

In a preferred use, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine, acetylated to N-acetylmannosamine and the latter is allowed to react with pyruvate in the presence of Neu5Ac aldolase to form N-acetyl-neuraminic acid which is converted into activated sialosides convenient for enzymatic or chemical synthesis of sialylated human milk oligosaccharides.

The eighth aspect of this invention is the use of the substituted D-mannosamine derivatives of formula 1 and their salts for the synthesis of viral neuraminidase inhibitors like zanamivir and analogues thereof [31]. Accordingly, substituted D-mannosamine derivatives of formula 1 and salts thereof are reduced to mannosamine, acetylated to N-acetylmannosamine or transformed to other derivatives that are substrate for aldolases and allowed to react with pyruvate in the presence of aldolase to form N-acetyl-neuraminic acid according to the seventh aspect. The carboxyl group is blocked in the form of an ester and the hydroxyls are protected preferably by acyl groups using known methods. The glycosidic OH-group is converted into an aglycon that can be easily subjected to β-elimination resulting in the formation of C2-C3 unsaturation. Such a group can be e.g. halogen, alkyl- or arylthio, acyloxy, or imidate, which readily undergoes β-elimination on treatment with a base or under flash vacuum pyrolysis (see e.g. ref. [32] and references cited therein). The resulting glycol-type compound is then manipulated at C-4 to introduce a nitrogen function such as an azido group with retention of configuration, which then can be easily transformed into an amino or a guanidino group giving rise to zanamivir or related derivatives after the ultimate deprotection steps (refs. [33,34] and references cited therein).

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used in the synthesis of zanamivir.

The ninth aspect of this invention relates to the method of synthesis of substituted D-mannosamine derivatives of formula 1 and salts thereof for the synthesis of free D-mannosamine and/or salts thereof. The method is based upon the utilisation of substituted D-mannosamine derivatives of formula 1 and salts thereof, wherein the $R_1$ (and, where present, $R_3$) is removed by hydrogenolysis in a catalytic hydrogenation reaction (Scheme 1). This reaction typically takes place in a protic solvent or in a mixture of protic solvents. The protic solvent can be water, acetic acid or a $C_1$-$C_6$ alcohol. A mixture of one or more protic solvents with one or more suitable aprotic organic solvents partially or fully miscible with the protic solvent(s) (such as THF, dioxane, ethyl acetate or acetone) can also be used. Water, one or more $C_1$-$C_6$ alcohols or a mixture of water and one or more $C_1$-$C_6$ alcohols are preferably used as the solvent system. Solutions containing the carbohydrate derivatives in any concentration or suspensions of the carbohydrate derivatives in the solvent(s) used are also applicable. The reaction mixture is stirred at a temperature in the range of 10-100° C., preferably between 20-50° C., in a hydrogen atmosphere of 1-50 bar (100 to 5000 kPa) in the presence of a catalyst such as palladium, Raney nickel or any other appropriate metal catalyst, preferably palladium on charcoal or palladium black, until reaching the completion of the reaction. Transfer hydrogenation can also be performed, when the hydrogen is generated in situ from cyclohexene, cyclohexadiene, formic acid or ammonium formate. Addition of organic or inorganic bases or acids and/or basic and/or acidic ion exchange resins can also be used to improve the kinetics of the hydrogenolysis. The use of basic substances is especially preferred when starting from a compound of formula 1A when halogen substituents are present on the substituted benzyl moieties of the precursors and/or the formation of mannosamine base is desirable. Preferred organic bases include, but are not limited to, triethylamine, diisopropyl ethylamine, ammonia, ammonium carbamate and diethylamine. An organic or an inorganic acid is favourably used as a co-solvent or additive in cases when mannosamine salts are the intended products. Preferred acids include, but are not limited to, formic acid, acetic acid, propionic acid, chloroacetic acid, dichloroacetic acid, trifluoroacetic acid, HCl and HBr. When starting from a compound of formula 1B, an acid must be used, while the hydrolysis and the hydrogenolysis simultaneously take place. The conditions proposed above allow simple, convenient and delicate removal of the solvent(s) giving rise to pure mannosamine or its salt.

If mannosamine in the form of its free base is formed in the reductive step it can be converted into its acid-addition salt. The salt formation is typically carried out in solution using inorganic or organic acids or salts. Solvents including, but not limited to, acetone, water, dioxane, DMSO, THF, DMF, alcohols, MeCN, and mixtures of thereof can be used for such a transformation. Suitable inorganic acids include, but are not limited to, HCl, $H_2SO_4$, $HNO_3$ and $H_3PO_4$, in concentrated form or diluted in water or other solvents such as methanol, ethanol or dioxane. Suitable organic acids include, but are not limited to, formic acid, acetic acid and oxalic acid. The salts of these acids with a base whose basicity is weaker than that of mannosamine can be used as well. The product is typically obtained by selective precipitation by adding apolar solvents such as diethyl ether, diisopropyl ether, acetone or alcohols, or by crystallization in high yield. Chromatography is not necessary.

In a preferred embodiment, compounds of formula 1, wherein $R_1$ (and, where present, $R_3$) is a benzyl or naphthylmethyl group optionally substituted with one or more groups selected from phenyl, alkyl or halogen, and more preferably wherein $R_1$ (and, where present, $R_3$) is a benzyl group, are used for the synthesis of free D-mannosamine and/or salts thereof. These preferred and more preferable protecting groups have the advantage that the by-products of the hydrogenolysis are exclusively toluene, methylnaphthalene, or substituted toluene or methylnaphthalene derivatives, respectively. Such by-products can easily be removed even in multi ton scales from water soluble saccharide products via evaporation and/or extraction processes.

According to another embodiment, the mixture of N-benzyl/substituted benzyl-D-mannosamine and -glucosamine obtained according to the second and third aspects, or the mixture of N,N'-disubstituted 1,2-diamino-1,2-dideoxy-D-mannosamine and -glucosamine obtained according to the third aspect is subjected to catalytic hydrogenolysis in the presence of acid, preferably HCl, to yield a mixture of D-mannosamine hydrochloride and D-glucosamine hydrochloride, the components of which can be separated by selective crystallization leading to pure D-glucosamine hydrochloride and pure D-mannosamine hydrochloride.

The tenth aspect of this invention relates to the method of synthesis of D-mannosamine-derived synthons (that is, mannosamine derivatives that can be used for the synthesis of mannosamine-containing compounds such as oligo- or polysaccharides).

N-Acetyl-D-mannosamine in oligo- or polysaccharides is preferably linked with a β-linkage. In order to achieve a β-interglycosidic link, two main routes have been developed: an indirect route in which glucopyranosyl, gluculopyranosyl or gluculopyranosyl oxime donors are first used to build the β-linkage and the reconstruction of the mannosamine unit is made after the formation of the β-linkage; and a direct route in which a suitable D-mannosaminyl donor is employed [21]. The latter route requires a non-participating group in position 2 of the D-mannosaminyl donor, and among such possible synthons only 2-azido-2-deoxy-D-mannopyranosyl derivatives have proved to have synthetic relevance. These glycosyl donors can be synthetized via complicated multistep pathways starting from D-glucose. However, the substituted D-mannosamine derivatives of formula 1 and salts thereof of the invention can easily be converted into such mannosaminyl donors. Thus, the free amine, obtained by removal of the $R_1$-group (and, where present, the $R_3$-group) according to the ninth aspect of the invention, can be subjected to a diazo transfer reaction with triflic azide to covert the amino group to azido [22]. This conversion can also be performed on mannosamine O- or S-glycosides that are suitable for glycosyl coupling (e.g. alkyl or aryl thioglycosides, O-pentenyl glycoside, see ref [23]). The resulting 2-azido-2-deoxy-D-mannopyranose derivatives can be subjected to reactions to protect the 3,4,6-positions (ethers, esters, acetals) and after appropriate anomeric activation (thioglycosides, acetates, benzoates, trichloroacetimidates, glycosyl halides) they are considered to be useful synthons in interglycosidic coupling reactions to transfer β-mannosaminyl moiety.

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used for the synthesis of mannosamine which is then subsequently converted into D-mannosamine-derived synthons practical for the manufacture of mannosamine containing oligosaccharides.

The eleventh aspect of this invention relates to the method of synthesis of other D-mannosamine-derived synthons starting from the substituted D-mannosamine derivatives of formula 1 and salts thereof of the invention. Thus, the amino group of mannosamine, which compound is obtained by removal of the $R_1$-group (and, where present, the $R_3$-group) according to the fourth aspect of the invention, can be masked with a protective group before glycosylation reactions. Suitable protective groups can be, for instance, phthalyl, tetrachlorophthalyl, dithiasuccinoyl, trifluoroacetyl, trichloroacetyl, dimethylmaleolyl, trichloroethoxycarbonyl or allyloxycarbonyl group, all of which are readily used in glycosylation reactions. These groups can be introduced by the reaction of the amine with the activated acyl derivatives, such as anhydrides, halogenides or active esters, in the presence of a base, except for the dithiasuccinoyl group which can be formed via a two-step sequence (ethoxythiocarbonylation followed by cyclization with chlorocarbonylsulfenyl chloride). The resulting 2-acylamino-2-deoxy-D-mannopyranose derivatives can be subjected to reactions to protect the 3,4,6-positions (ethers, esters, acetals) and after appropriate anomeric activation (thioglycosides, acetates, benzoates, trichloroacetimidates, glycosyl halides) they are considered to be useful synthons in interglycosidic coupling reactions to transfer a β-mannosaminyl moiety.

The twelfth aspect of the invention relates to the method of synthesis of D-mannosamine containing oligosaccharides. Some pathogenic bacteria like *Neisseria meningitidis, Haemophylus influenzae* or *Streptococcus pneumoniaie* have capsular polysaccharides that contain 2-acetamido-2-deoxy-β-D-mannopyranosyl or -mannopyranuronic acid structural units (see e.g. ref [24]). The recognition that the capsular polysaccharides present on the surface of bacteria are associated with the bacteria's virulence factor led to development of capsular polysaccharide vaccines licensed for the use in the immunoprophylaxis of diseases caused by the above-named microorganisms [25]. The chemical synthesis of these antigens requires the introduction of the mannosaminyl unit into a certain position of the oligo- or polysaccharide chain. After anomeric activation, the mannosaminyl building blocks obtained from substituted D-mannosamine derivatives of formula 1 and salts thereof by hydrogenolysis and subsequent conversion to suitable glycosyl donors as described above are allowed to react with an appropriate acceptor under glycosylation conditions. The term "glycosylation conditions" means in the present context to run the reaction in an aprotic solvent or in a mixture of aprotic solvents in the presence of an activator so as to lead to the desired glycosylated product by controlling the stereoselectivity of the conjugation via non-neighbouring group active protecting group strategy, solvent effect, halide effect, promoter selection and temperature control. In the case of carbohydrates, an array of anomeric activation and promoter design for glycosylation has been developed and is available to a skilled person engaged in synthetic carbohydrate chemistry. These methodologies are expansively discussed by reviews and handbooks, for instance by A. V. Demchenko (ed.): *Handbook of Chemical Glycosylation*, Wiley-VCH, 2008. For completeness, some general considerations are briefly mentioned below depending on the anomeric substituent (the protecting groups of the acceptors and donors remain intact under glycosylation).

The glycosyl halides (aglycon means F, Cl, Br, I) are frequently used in glycosylation reactions because of their easy accessibility and satisfactory reactivity. Typically, anomeric halides follow the reactivity order F<Cl<Br<I for nucleophilic displacement. The glycosylation reactions are generally promoted by heavy metal ions, mainly mercury or silver, and Lewis acids. Glycosyl trichloroacetimidates (aglycon is —OC(=NH)CCl$_3$) in typical glycosylation reactions can be promoted by catalytic amount of Lewis acid, such as trimethylsilyl triflate or BF$_3$-etherate. Glycosyl acetates or benzoates (aglycon represents —OAc or —OBz) in glycosylation reactions are first subjected to electrophilic activation providing a reactive intermediate, then treated with the nucleophilic OH-acceptor. Typical activators of choice are Brønsted acids (such as p-TsOH, HClO$_4$ or sulfamic acid), Lewis acids (such as ZnCl$_2$, SnCl$_4$, triflate salts, BF$_3$-etherate, trityl perchlorate, AlCl$_3$ or triflic anhydride) and their mixtures. Pentenyl glycosides (aglycon means —O—(CH$_2$)$_3$—CH=CH$_2$) as glycosyl donors can be transglycosylated with appropriate glycosyl acceptors in the presence of a promoter such as NBS and NIS. Protic or Lewis acids (triflic acid, Ag-triflate, etc.) can enhance the reaction. Thioglycosides (aglycon denotes alkylthio- or optionally substituted phenylthio-group) can be activated by thiophilic promoters such as mercury(II) salts, Br$_2$, I$_2$, NBS, NIS, triflic acid, triflate salts, BF$_3$-etherate, trimethylsilyl triflate, dimethyl-methylthio sulphonium triflate, phenylselenyl triflate, iodonium dicollidine perchlorate, tetrabutylammonium iodide or mixtures thereof, in condensation reactions, preferably by Br$_2$, NBS, NIS or triflic acid.

In order to construct oligo- or polysaccharides, the mannosaminyl containing structural disaccharide unit obtained above needs to be transformed further. These reactions can involve selective protection/deprotection manipulations of the OH-groups, the conversion of the azido or protected amino group to N-acetyl, anomeric activation of the reducing end for additional cross-coupling with acceptors, and optionally the selective oxidation of the primary OH-group in the mannosamine unit in the case of 2-acetamido-2-deoxy-β-D-mannopyranuronic acid residue containing oligomers, depending on whether the synthons will be used as donor, acceptor or both. These reactions are within the routine skill of a practitioner trained in carbohydrate chemistry, and discussed or summarized by numerous handbooks and reviews, e.g. S. Hanessian: *Preparative Carbohydrate Chemistry*, Marcel Dekker, 1997; M. L. Sinnot: *Carbohydrate Chemistry and Biochemistry*, RSC Publishing, 2007; D. E. Levy, P. Fügedi (eds.): *The Organic Chemistry of Sugars*, Taylor & Francis, 2006; T. K. Lindhorst: *Essentials of Carbohydrate Chemistry and Biochemistry*, Wiley-VCH, 2007.

In a preferred embodiment compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used for the synthesis of D-mannosamine containing oligosaccharides. This synthesis comprises the steps of reduction of the compound of formula 1 as defined above to mannosamine, subsequent conversion of the mannosamine into D-mannosamine building blocks, glycosylation reaction between the building blocks and appropriate glycosyl acceptors, and further functional group manipulations, glycosylation reactions and deprotection in order to give rise to D-mannosamine containing oligosaccharides.

The thirteenth aspect of this invention relates to the method of synthesis of N-acetyl-D-mannosamine (ManNAc) and its O-glycosides. N-Acetyl-D-mannosamine is of high importance as being the biosynthetic precursor of sialic acid. Furthermore, ManNAc and its methyl α- and β-glycosides, both as pyranoside and furanoside, have been proved to trigger antibody-like activity of immunoglobulin derived from mouse plasmacytoma [26].

In the production of N-acetyl-D-mannosamine starting from N-acetyl-D-glucosamine by epimerization, initiated with either base or epimerase enzyme, an equilibrium mixture has been reached which poses isolation and purification problems. This problem can be overcome using substituted D-mannosamine derivatives of formula 1 provided by the invention, which can be reduced with catalytic hydrogenation (see the above ninth aspect) and the resulting mannosamine can be transformed into the N-acetyl derivative in two ways (Scheme 2). The first method is selective N-acetylation in the presence of one or more hydroxyls, which is a well-known reaction within the skilled person's general knowledge. It involves treatment of the mannosamine with acetic anhydride, acetyl halogenide or another appropriate acetyl transfer reagent known in the art, typically acetic anhydride or acetyl chloride. The reaction can be carried out in solution in the presence or absence of a base. Solvents including, but not limited to, acetone, water, dioxane, DMSO, THF, DMF, alcohols, MeCN, and mixtures thereof can be used for such a chemical transformation. A suitable base for use in the reaction is an inorganic base (such as $K_2CO_3$, $Na_2CO_3$ or $NaHCO_3$) or an organic base (such as pyridine, triethylamine or Hünig's base). The set temperature of the reaction can be between −10° C. up to the reflux temperature of the solvent(s). The reaction time typically varies from 30 min to 2 days depending on the structures, the set temperature and the nature of the reactive agent. The skilled practitioner knows how to drive the reaction in order to acetylate the amino portion while the OH-groups remain unaffected. Any eventually formed overacetylated by-product(s) can be readily transformed into ManNAc with e.g. NaOH/MeOH or NaOMe/MeOH treatment. The second method is a peracetylation followed by a de-O-acetylation. The peracetylation can be carried out in solution with an acylating agent in the presence or absence of a base. Solvents including, but not limited to, acetone, dioxane, DMSO, THF, DMF, alcohols, MeCN, and mixtures thereof can be used for such a chemical transformation. A suitable base for use in the reaction is an inorganic base (such as $K_2CO_3$, $Na_2CO_3$, $NaHCO_3$ or NaOH) or an organic base (such as pyridine, triethylamine or Hünig's base). A suitable acylating agent is an activated acetic acid derivative known in the art, and typically acetic anhydride and acetyl chloride are used as the acylating agent. The set temperature of the reaction can be between −10° C. up to the reflux temperature of the solvent(s). The reaction time typically varies from 30 min to 2 days depending on the structures, the set temperature, and the nature of the reactive agent. The skilled person knows how to drive the reaction until all of the functional groups are acetylated. The de-O-acetylation reaction can be carried out in solution in the presence of a base. If the base used for the reaction is an inorganic strong base (such as $K_2CO_3$, LiOH, NaOH, KOH or $Ba(OH)_2$), the solvents of choice are water, alcohol or water-organic solvent (such as acetone, dioxane, DMSO, THF, DMF, alcohols, MeCN) mixture. If an alcoholate (such as NaOMe, NaOEt or KO$^t$Bu) is chosen as the base, the solvent needs to be the corresponding alcohol (e.g. NaOMe/MeOH). The set temperature of the reaction can be between 0° C. up to the reflux temperature of the solvent(s). The reaction time typically varies from 30 min to 1 day depending on the structures, the set temperature, and the nature of the reactive agent.

The reduction-acetylation sequence can be performed in separate elementary steps with the isolation of the intermediate free mannosamine in crystalline form, or conducted in one pot with the acetylation of the crude debenzylated mannosamine. Both methods provide pure crystalline N-acetyl-mannosamine in high yield. If desired, N-acetylmannosamine can be converted into the corresponding O-glycoside in a known manner.

In a preferred use compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine and acetylated to ManNAc.

Continuing the thirteenth aspect of the invention, the fourteenth aspect relates to the method of synthesis of neuraminic acid derivatives, including sialic acid and salts thereof.

Neuraminic acids are derivatives of the nine-carbon sugar 5-amino-3,5-deoxy-D-glycero-D-galacto-nonulosonic acid, particularly N-acetyl-(Neu5Ac) and N-glycolyl-neuraminic acid (Neu5Gc), which can be substituted at C-4, C-7, C-8 and C-9 by various moieties. They have many major biological roles, ranging from embryogenesis to neural plasticity to pathogen interactions. Although they can rarely occur in free form, they are usually found in chemical covalent linkage at the non-reducing terminus or in internal positions of oligosaccharide side-chains of glycoproteins and glycolipids. The linkages of sialic acids in which they are bound to penultimate sugars such as galactose, N-acetyl-galactosamine and N-acetyl-glucosamine are most commonly α-2,3- and α-2,6-ketosidic bonds.

N-Acetyl-neuraminic acid is commonly produced by enzymatic pathways, either from ManNAc and pyruvate by means of a Neu5Ac aldolase or in a two-enzyme sequential system where N-acetylglucosamine is epimerized on the action of a GlcNAc 2-epimerase and the in situ obtained ManNAc reacts further with pyruvate in the presence of a Neu5Ac aldolase (see e.g. ref [27] and references cited therein).

N-Acetylmannosamine provided in high purity according to the thirteenth aspect of the invention can be used in the manufacture of neuraminic acid derivatives, preferably Neu5Ac, in enzymatic system. Generally, the aldol condensation is performed with a large, usually 7-10 fold, excess of pyruvate in order to drive the reaction toward product formation and maximize the consumption of ManNAc. The reaction can also be conducted in a continuous reactor. The product is mainly isolated by ion exchange chromatography from the unreacted ManNAc and pyruvate. The isolation steps can be simplified with the use of pyruvate decarboxylase, which catalyses the decomposition of excess pyruvic acid into the volatile acetaldehyde and carbon dioxide [28]. The resulting Neu5Ac can be transformed into other naturally occurring neuraminic acid derivatives by common chemical modifications. Moreover, as the aldolase enzyme accepts a broad range of substrates, mannosamine, N-glycolylmannosamine or other mannosamine derivatives, all of them available by simple conversion starting from substituted D-mannosamine derivatives of formula 1 and salts thereof, can serve as basis for synthesizing many natural and non-natural neuraminic acid derivatives by enzymatically directed aldol condensation reactions.

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine, acetylated to N-acetylmannosamine and allowed to react with pyruvate in the presence of Neu5Ac aldolase to form N-acetyl-neuraminic acid.

The fifteenth aspect of this invention relates to the method of synthesis of neuraminic acid derivatives containing oligo- or polysaccharides, preferably sialoglycoconjugates.

Among sialoglycoconjugates, sialylated human milk oligosaccharides like 3'-sialyllactose, 6'-sialyllactose, 3'-sialyl-3-fucosyllactose, sialyllacto-N-tetraoses, sialyl-fucosyl-lacto-N-tetraoses, disialyllacto-N-tetraose, sialyllacto-N-fucopentaose, monosialyllacto-N-hexaose, monofucosyl-monosialyllacto-N-hexaose, mono fucosyl-monosialyllacto-N-neohexaose, mono fucosyl-disialyllacto-N-neohexaose etc. are of great importance which is directly linked to their unique biological activities such as antibacterial, antiviral, immune system and cognitive development enhancing activities. Sialylated human milk oligosaccharides are found to act as prebiotics in the human intestinal system helping to develop and maintain the intestinal flora. Furthermore they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics. In the human milk oligosaccharides the sialic acid residue is always linked to the terminal 3-O- and/or 6-O-position(s) of D-galactose via α-glycosidic linkage.

Generally, the synthesis of complex sialooligosaccharides follows multistep synthetic pathways, is conducted in enzymatic systems or combines both. Whatever route is taken, neuraminic/sialic acid derivatives suitably armed with protective groups and activated on the anomeric centre or neuraminyl/sialyl glycosides that are substrates for enzymes capable of transferring a neuraminyl/sialyl moiety are needed in order to couple them to the host molecule.

Accordingly, substituted D-mannosamine derivatives of formula 1 and salts thereof are reduced to mannosamine, then acetylated to N-acetylmannosamine or transformed to other derivatives that are substrates for aldolases, are allowed to react with pyruvate in the presence of aldolase to form N-acetyl-neuraminic acid or other neuraminic acid derivatives as disclosed above, which then can be converted into the desired sialyl/neuraminyl donors by known methodologies. In chemical glycosylation, the secondary OH-groups, the amino grouping and the carboxylic portion have to be in protected form for which purpose an array of protecting groups, mainly esters, ethers and acetals, are available to the skilled person. Among OH— protection possibilities, optionally substituted acyls, such as acetyl, benzoyl, chloroacetyl or chlorobenzoyl, and ether-type groups such as benzyl are of synthetic usefulness; the carboxyl group can be protected by an ester, typically by a methyl or benzyl ester; and the amino function can be masked in form of an azide, diacetyl, trifluoroacetyl, trichloroacetyl, Troc, Fmoc or phthalimide group, or as a cyclic carbamate with the adjacent 4-OH. The anomeric centre substitution can be varied among halo, alkyl- or arylthio, dialkyl phosphite or trihaloacetimidate, each of which is commonly used in sialoglycosylation methods. The protective group introduction and anomeric centre activations mentioned above can be carried out by known processes (see e.g. refs. [29,30] and references cited therein). The skilled man involved in carbohydrate chemistry, especially in sialochemistry, is able to select which protective groups and anomeric agylcons in the sialic donor are suitable in order to conduct the glycosylation reaction with the high probability of a preferable outcome including yield, anomeric ratio and by-product formation. These factors depend on promoter design, solvent effect, reaction condition, acceptor structure, etc. For enzymatic sialotransfer processes the appropriate substrates for the enzymes (e.g. CMP-sialic acid for sialyltransferases, 2-O-(p-nitrophenyl)- or 2-O-(4-methylumbeliferyl)-α-D-sialosides for transsialidases) are easily accessible from the neuraminic/sialic acid derivatives obtained by the above method.

In a preferred use, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are reduced to mannosamine, acetylated to N-acetylmannosamine and the latter is allowed to react with pyruvate in the presence of Neu5Ac aldolase to form N-acetyl-neuraminic acid which is converted into activated sialosides convenient for enzymatic or chemical synthesis of sialylated human milk oligosaccharides.

The sixteenth aspect of this invention provides a method of synthesis of viral neuraminidase inhibitors like zanamivir and analogues thereof [31]. Accordingly, substituted D-mannosamine derivatives of formula 1 and salts thereof are reduced to mannosamine, acetylated to N-acetylmannosamine or transformed to other derivatives that are substrate for aldolases and allowed to react with pyruvate in the presence of aldolase to form N-acetyl-neuraminic acid according to the thirteenth aspect. The carboxyl group is blocked in the form of an ester and the hydroxyls are protected preferably by acyl groups using known methods. The glycosidic OH-group is converted into an aglycon that can be easily subjected to β-elimination resulting in the formation of C2-C3 unsaturation. Such a group can be e.g. halogen, alkyl- or arylthio, acyloxy, or imidate, which readily undergoes β-elimination on treatment with a base or under flash vacuum pyrolysis (see e.g. ref. [32] and references cited therein). The resulting glycal-type compound is then manipulated at C-4 as to introduce a nitrogen function such as an azido group with retention of configuration, which then can be easily transformed into an amino or a guanidino group giving rise to zanamivir or related derivatives after the ultimate deprotection steps (refs. [33,34] and references cited therein).

In a preferred embodiment, compounds of formula 1, wherein $R_1$ (and, where present, $R_3$) is a benzyl or naphthylmethyl group optionally substituted with one or more groups selected from phenyl, alkyl or halogen, and wherein $R_1$ (and, where present, $R_3$) is more preferably a benzyl group, are used in the synthesis of zanamivir.

It will be appreciated that the method features of aspects ten to seventeen can be combined with the method of the second and third aspects of the invention to form entire methods of formation of the compounds indicated in the tenth to seventeenth aspects.

Other features of the invention will become apparent from the following examples which are for illustrating and not for limiting the invention.

EXAMPLES

Example 1

N,N'-dibenzyl-1,2-diamino-1,2-dideoxy-D-mannopyranose

To a mixture of D-(−)-fructose (50 g, 277.5 mmol) in benzyl amine (100 ml) was added benzyl ammonium chloride (30 g, 208 mmol) at room temperature. The mixture was stirred for 6 hours, at which time ethanol (50 ml) was added to make the mixture homogenous. After stirring overnight, another portion of ethanol (50 ml) was added resulting in a homogenous mixture. After 2 hours, water (150 ml) was added and the stirring was continued for 3 hours. The resulting suspension was separated by filtration, and the filtered material was washed with cold aqueous ethanol and dried under vacuum to constant weight, giving 21.3 g of title compound as a white solid. The mother liquor contained N,N'-dibenzyl-1,2-diamino-1,2-dideoxy-D-mannopyranose along with N,N'-dibenzyl-1,2-diamino-1,2-dideoxy-D-glucopyranose.

M.p.: 105-111° C., purity: >95% (by HPLC).

$^1$H NMR (600 MHz, DMSO) δ: (mixture of α- and β-anomers) H-1 3.90 and 4.40, $C_1$—NH 2.60, 2.98 and 3.11, $C_1$—NH—$CH_2$ 3.68, 3.77, 3.79 and 4.00, Ph 7.16-7.40, H-2 2.77 and 2.82, $C_2$—NH 1.80, 2.00 and 2.09, $C_2$—NH—$CH_2$ 3.74, 3.88 and 4.08, Ph 7.16-7.40, H-3 3.43 and 3.67, $C_3$—OH 4.66 and 4.74, H-4 3.27 and 3.30, $C_4$—OH 4.66 and 4.71, H-5 2.94 and 3.45, H-6 3.48, 3.49, 3.58 and 3.68, $C_6$—OH 4.30 and 4.34.

$^{13}$C NMR (125 MHz, DMSO) δ: (mixture of α- and β-anomers) C-1 83.6 and 87.3, $C_1$—NH—$CH_2$ 48.1 and 48.2, C-2 60.4 and 61.5, $C_2$—NH—$CH_2$ 50.7 and 53.9, C-3 70.0 and 75.6, C-4 67.7 and 68.0, C-5 71.9 and 78.2, C-6 61.1 and 61.3, Ph 141.9, 141.1, 140.9, 140.8, 128.1, 128.0, 127.9, 127.7, 126.6 and 126.4.

Example 2

N-benzyl-2-amino-2-deoxy-D-mannose

A) Typical procedure from fructose: 18.0 g (100 mmol) of D-(−)-fructose was treated at 0° C. with freshly distilled benzyl amine (3-8 equiv.). The reaction mixture was allowed to warm to room temperature and was then heated at 40° C. for 20 h. The TLC (dichloromethane:methanol:ammonium hydroxide 2:1:1) showed the disappearance of the starting material. The excess of benzyl amine was removed by repeated washings with petroleum ether according to the following method: 150-500 mL of petroleum ether was added into the reaction mixture and subsequently cooled to between −25 and −20° C. (dry ice-alcohol bath) until the carbohydrate-rich phase was frozen. The organic layer was then decanted, and the procedure was repeated 4-5 times. The obtained crude fructosyl amine was diluted with methanol (200-300 mL) and treated with glacial acetic acid (15-20 mL) at room temperature for 2-4 h. TLC (dichloromethane:methanol:ammonium hydroxide 20:4:0.5) showed consumption of the ketosylamine and the formation of N-benzyl-2-amino-2-deoxy-D-mannose together with N-benzyl-2-amino-2-deoxy-D-glucose in a ratio of 2:8-4:6 as the main products. The solvent was evaporated under reduced pressure and the residue purified by column chromatography (dichloromethane:methanol:ammonium hydroxide 20:4:0.5) to give N-benzyl-2-amino-2-deoxy-D-mannose as an amorphous solid (4.1-8.6 g).

$^1$H NMR (600 MHz, DMSO) δ: α-anomer H-1 5.02 dd, $C_1$—OH 6.21 d, H-2 2.69 dd, NH 1.97 br, $CH_2$ 3.82, 3.70 d, Ph 7.17-7.40 m, H-3 3.66 m, $C_3$—OH 4.50 d, H-4 3.32 m, $C_4$—OH 4.67 d, H-5 3.51 m, H-6×3.47 m, H-6y 3.62 m, $C_6$—OH 4.36 t; β-anomer H-1 4.95 dd, $C_1$—OH 6.15 d, H-2 2.89 t, NH 2.22 br, $CH_2$ 3.79, 3.68 d, Ph 7.17-7.40 m, H-3 4.10 m, $C_3$—OH 4.50 br, H-4 3.67 m, $C_4$—OH 4.76 br, H-5 3.77 m, H-6×3.33 m, H-6y 3.57 m, $C_6$—OH 4.35 t.

$^{13}$C NMR (125 MHz, DMSO) δ: α-anomer C-1 91.3, C-2 61.4, $CH_2$ 51.8, Ph 141.0, 128.1, 127.9, 126.6, C-3 69.6, C-4 67.7, C-5 72.6, C-6 61.4; β-anomer C-1 101.5, C-2 68.0, $CH_2$ 51.2, Ph 140.7, 128.1, 127.9, 126.6, C-3 69.0, C-4 69.5, C-5 80.3, C-6 63.6.2.

B) From compound of example 1: to a suspension of N,N'-dibenzyl-1,2-diamino-1,2-dideoxy-D-mannopyranose (10 g) in methanol (30 ml) conc. HCl-solution (4 ml) was gradually added and the mixture was heated to 40° C. for 2-3 hours. The solvent was carefully evaporated, the residue was taken up in methanol and evaporated again 3-4 times. The resulting solid was suspended in ethanol and heated to reflux, the insoluble material was removed by hot filtration, and the filtrate was evaporated to dryness to yield the hydrochloride salt of N-benzyl-2-amino-2-deoxy-D-mannose.

Example 3

D-mannosamine hydrochloride

A) The crude mixture of N-benzyl-2-amino-2-deoxy-D-mannose and N-benzyl-2-amino-2-deoxy-D-glucose obtained according to example 2A was suspended in methanol (20-100 mL), and the pH was adjusted to approximately 1-2 with HCl (10-40 mL 2M HCl and additional 2-8 mL conc. HCl). 10% Pd on charcoal (0.4-1.6 g) was added and the reaction mixture was stirred at r.t. or at 45° C. under $H_2$-atmosphere (up to 5 bar) until all the starting material was consumed. The reaction mixture was filtered through Celite® and washed with 20-50 mL of methanol:water (2:1). The solvents were evaporated until approx. 20-40 mL of volume remained. The crystallization of glucosamine hydrochloride was initiated by adding methanol (40-80 mL) to the aqueous sugar solution and kept at 0-5° C. for overnight. The crystals were separated by filtration and washed with cold methanol. Methanol from the mother liquor was evaporated, and to the remaining aqueous solution 20-80 mL isopropanol was added. The solution was kept at 0-5° C. overnight, the crystals formed were filtered, washed with cold isopropanol and dried: 3.9 g of D-mannosamine hydrochloride was isolated.

B) To 12.0 g of N-benzyl-mannosamine of example 2A was added a suspension of 10% Pd/C (0.5 g) in 20 ml water. The pH of the reaction mixture was adjusted to 4-4.5 with 10% HCl solution. The reaction mixture was stirred for 6 hours at 40° C. under $H_2$ pressure (2.5 bar). The pH was then adjusted to 3 with 10% HCl solution. The reaction mixture was kept unstirred overnight so that the catalyst could settle down (the catalyst remains in the reactor). The catalyst was filtered off and washed with a small amount of methanol:water (2:1). The methanol was removed in vacuo and replaced by 15 mL isopropanol. The isopropanol was distilled off and the same procedure was repeated again. To the reaction mixture, 30 ml iPrOH was added and the product crystallized overnight at 4° C. The crystals were filtered and washed with 5-8 mL isopropanol. The wet product was dried at room temperature, to give 8.4 g of D-mannosamine hydrochloride.

C) To a suspension of 10 g of N,N'-dibenzyl-1,2-diamino-1,2-dideoxy-D-mannopyranose in 30 mL methanol, 4 mL concentrated HCl was gradually added. The reaction mixture was heated to 40° C. and stirred at this temperature until completion. 10% Pd on charcoal was added as a suspension in 1 mL water. The reaction mixture was placed under $H_2$, pressurized to an absolute pressure of 2.5 atm (253 kPa) and heated to 40° C. for 3 hours. The catalyst was then filtered off and washed once with 3 mL methanol:water (2:1). The methanol was removed in vacuo and replaced several times with 10-15 mL isopropanol that was distilled off each time until crystals formed. When crystals formed, the solvent distillation was stopped, and the reaction mixture was stirred at 4° C. for at least 5 hours. The crystals of D-mannosamine hydrochloride were filtered and washed with 2 mL isopropanol and then recrystallized in 2 volumes of ethanol, refluxed for 3-5 minutes and filtered hot.

Example 4

N-acetyl-D-mannosamine

A suspension of 10.0 g D-mannosamine hydrochloride of example 3 in 30 ml ethanol:water (6:1) mixture was cooled to 0° C., and triethylamine (1.2 equiv.) was added at the same temperature. Acetic anhydride (1.2 equiv.) was added dropwise while the temperature was kept between 0-5° C. After completion of the addition (20-30 min), the reaction mixture was seeded with N-acetyl-D-mannosamine crystals and kept at 4° C. under stirring overnight. The crystals formed were filtered, washed and dried to give 9.65 g of N-acetyl-D-mannosamine.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. No acknowledgment of any prior published document herein should be taken to be an admission or representation that the teaching thereof was common general knowledge in Australia or elsewhere at the date hereof.

LIST OF REFERENCES

All references cited below, and all references mentioned in the text, are hereby incorporated by reference into the teachings of this invention.

[1] WO 2007/135086 A1
[2] S. Yamaguchi et al. *Trends Glycosci. Glycotechnol.* 18, 245 (2006)
[3] EP-A-385287
[4] A. Dondoni et al. *Tetrahedron Lett.* 33, 4221 (1992)
[5] A. Dondoni et al. *Chem. Eur. J.* 1, 505 (1995)
[6] J. C. Sowden et al. *Methods Carbohydr. Chem.* 1, 235 (1962)
[7] W. Roth et al. *J. Org. Chem.* 26, 2455 (1961)
[8] E. Kaji et al. *Bull. Chem. Soc. Jpn.* 61, 1291 (1988)
[9] Y. Tsuda et al. *Chem. Pharm. Bull.* 37, 2673 (1989)
[10] R. U. Lemieux et al. *Tetrahedron Lett.* 6, 4221 (1965)
[11] H. Paulsen et al. *Carbohydr. Res.* 136, 153 (1985)
[12] R. Bodner et al. *J. Org. Chem.* 70, 3988 (2005)
[13] J. Calveras et al. *Tetrahedron* 66, 4284 (2010)
[14] K. Takeda et al. *Tetrahedron Lett.* 33, 7145 (1992)
[15] T. M. Wrodnigg et al. *Topics Curr. Chem.* 215, 115 (2001)
[16] J. F. Carson J. Am. Chem. Soc. 78, 3728 (1956)
[17] DE 935009; U.S. Pat. No. 2,884,411
[18] K. Heyns et al. *Chem. Ber.* 88, 1551 (1955)
[19] P. S. Piispanen et al. *J. Org. Chem.* 68, 628 (2003)
[20] L. Chen et al. *Tetrahedron Lett.* 43, 2705 (2002)
[21] V. Pozsgay, in *Carbohydrates in Chemistry and Biology*, ed. B. Ernst, B. W. Hart, P. Sinaÿ, Wiley-VCH, Weinheim, 2000, Part I, Vol. 1, p. 318
[22] A. Vasella et al. *Helv. Chim. Acta* 74, 2073 (1991)
[23] T. Buskas et al. *Tetrahedron: Asym.* 5, 2187 (1994)
[24] H. J. Jennings *Adv. Carbohydr. Chem. Biochem.* 41, 155 (1983)
[25] R. K. Sood et al. *Drug Discovery Today* 1, 381 (1996)
[26] L. Rovis et al. *Carbohydr. Res.* 23, 223 (1972)
[27] T-H. Wang et al. *BMC Biotechnology* 9:63 (2009)
[28] T. Sugai et al. *Bull. Chem. Soc. Jpn.* 68, 3581 (1995)
[29] D. K. Ress et al. *Curr. Org. Synth.* 1, 31 (2004)
[30] X. Chen et al. *ACS Chem. Biol.* 5, 163 (2010)
[31] M. von Itzstein et al. *Nature* 363, 418 (1993)
[32] E. J. Horn et al. *J. Org. Chem.* 74, 4357 (2009)
[33] M. von Itzstein et al. *Carbohydr. Res.* 244, 181 (1993)
[34] WO 2010/061182 A2

The invention claimed is:

1. A compound of the following formula 1 or a salt thereof

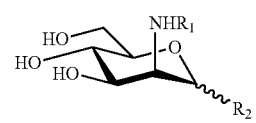

wherein $R_2$ is OH or $R_2$ is —$NHR_3$, and wherein $R_1$ and $R_3$ are each independently selected from the group consisting of: benzyl, diphenylmethyl (benzhydryl), 1-naphthylmethyl, 2-naphthylmethyl or triphenylmethyl (trityl) groups, each of which can optionally be substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen.

2. A compound according to claim 1 or a salt thereof, of the following formula 1A

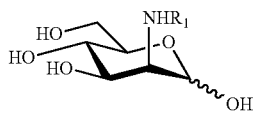

wherein $R_1$ selected from the group consisting of: benzyl, diphenylmethyl (benzhydryl), 1-naphthylmethyl, 2-naphthylmethyl or triphenylmethyl (trityl) groups, each of which can optionally be substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen.

3. A compound according to claim 1 or a salt thereof, of the following formula 1B

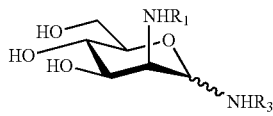

wherein $R_1$ and $R_3$ are each independently selected from the group consisting of: benzyl, diphenylmethyl (benzhydryl), 1-naphthylmethyl, 2-naphthylmethyl or triphenylmethyl (trityl) groups, each of which can optionally be substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen.

4. A method for the preparation of a compound of formula 1B of claim 3, comprising the steps: a) treating D-fructose with $R_1$—$NH_2$ and a salt thereof, wherein the salt is present in 0.2 to 1.0 equivalents in proportion to $R_1NH_2$, or wherein the treatment time is not more than 4 days, and b) separating the compound of formula 1B from the reaction mixture.

5. The method according to claim 4, wherein $R_1$—$NH_2$ is benzyl amine.

6. A method for the preparation of a compound of formula 1A of claim 2, comprising the steps of: a) treating D-fructose with $R_1$—$NH_2$ to yield a fructosyl amine derivative; b) isolating the fructosyl amine derivative as a crude product by separating excess $R_1$—$NH_2$ from it; and c) treating the crude fructosyl amine derivative with acid.

7. The method according to claim 6, wherein $R_1$—$NH_2$ is benzyl amine, and the reaction in step c) is conducted in methanol in the presence of glacial acetic acid.

8. A method for the preparation of a compound of formula 1A wherein $R_1$ is selected from the group consisting of: benzyl, diphenylmethyl (benzhydryl), 1-naphthylmethyl, 2-naphthylmethyl or triphenylmethyl (trityl) groups, each of which can optionally be substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen, comprising the steps of:
a) treating D-fructose with $R_1$—$NH_2$ and a salt thereof, wherein the salt is present in 0.2 to 1.0 equivalents in proportion to $R_1NH_2$, or the treatment time is not more than 4 days, b) separating the compound of formula 1B from the reaction mixture; and c) and treating the compound of 1B with acid to remove the —$NHR_3$ group.

9. A method of synthesizing D-mannosamine or a salt thereof, comprising the steps of: a) making a compound of formula 1B from D-fructose by the method according to claim 4; and b) hydrogenolysis of the compound of formula 1B to remove the groups $R_1$ and $R_3$.

10. A method of synthesizing N-acetyl-D-mannosamine, comprising the steps of:
i) synthesizing D-mannosamine according to the method of claim 9; and
ii) acetylating the amine group of the D-mannosamine to form N-acetyl-D-mannosamine.

11. A method of synthesizing N-acetyl neuraminic acid, comprising the steps of:
i) synthesizing N-acetyl-D-mannosamine according to the method of claim 10; and
ii) reacting the N-acetyl-D-mannosamine with pyruvate in the presence of an Neu5Ac aldolase.

12. A compound according to claim 2, or a salt thereof, wherein $R_1$ is a benzyl or naphthylmethyl group optionally substituted with one or more groups selected from phenyl, alkyl or halogen.

13. A compound according to claim 12, or a salt thereof, wherein $R_1$ is a benzyl group.

14. A compound according to claim 3, or a salt thereof, wherein $R_1$ and $R_3$ are each independently a benzyl or naphthylmethyl group optionally substituted with one or more groups selected from phenyl, alkyl or halogen.

15. A compound according to claim 14, or a salt thereof, wherein $R_1$ and $R_3$ are each a benzyl group.

16. A method of synthesizing D-mannosamine or a salt thereof, comprising the steps of: a) making a compound of formula 1A from D-fructose by the method according to claim 6; and b) hydrogenolysis of the compound of formula 1A to remove the group $R_1$.

17. A method of synthesizing D-mannosamine or a salt thereof, comprising the steps of: a) making a compound of formula 1B from D-fructose by the method according to claim 8; and b) hydrogenolysis of the compound of formula 1B to remove the groups $R_1$ and $R_3$.

18. A method of synthesizing N-acetyl-D-mannosamine, comprising the steps of:
i) synthesizing D-mannosamine according to the method of claim 16; and
ii) acetylating the amine group of the D-mannosamine to form N-acetyl-D-mannosamine.

19. A method of synthesizing N-acetyl-D-mannosamine, comprising the steps of:
i) synthesizing D-mannosamine according to the method of claim 17; and
ii) acetylating the amine group of the D-mannosamine to form N-acetyl-D-mannosamine.

20. A method of synthesizing N-acetyl neuraminic acid, comprising the steps of:
i) synthesizing N-acetyl-D-mannosamine according to the method of claim 18; and
ii) reacting the N-acetyl-D-mannosamine with pyruvate in the presence of an Neu5Ac aldolase.

21. A method of synthesizing N-acetyl neuraminic acid, comprising the steps of:
i) synthesizing N-acetyl-D-mannosamine according to the method of claim 19; and
ii) reacting the N-acetyl-D-mannosamine with pyruvate in the presence of an Neu5Ac aldolase.

22. A method for the preparation of a compound of formula 1B of claim 3, comprising the steps: a) treating D-fructose with $R_1$—$NH_2$ and a salt thereof, wherein the salt is present in 0.2 to 1.0 equivalents in proportion to $R_1NH_2$, and the treatment time is not more than 4 days, and b) separating the compound of formula 1B from the reaction mixture.

23. The method according to claim 22, wherein $R_1$—$NH_2$ is benzyl amine.

* * * * *

UNITED STATES PATENT AND TRADEMARK OFFICE
CERTIFICATE OF CORRECTION

PATENT NO. : 9,187,513 B2  
APPLICATION NO. : 14/111131  
DATED : November 17, 2015  
INVENTOR(S) : Ioannis Vrasidas et al.

Page 1 of 1

It is certified that error appears in the above-identified patent and that said Letters Patent is hereby corrected as shown below:

On title page, Item (75) Inventors, Line 1  
  replace "Salonika (GR)"  
  with --Thessaloniki (GR)--.

Signed and Sealed this  
Twelfth Day of April, 2016

Michelle K. Lee  
*Director of the United States Patent and Trademark Office*